United States Patent

Kobayashi et al.

[11] Patent Number: 4,513,316
[45] Date of Patent: Apr. 23, 1985

[54] AUTOMATIC SURFACE INSPECTION SYSTEM

[75] Inventors: Yuji Kobayashi, Fujisawa; Takao Okada, Kawasaki, both of Japan

[73] Assignees: Dai Nippon Printing Co., Ltd.; Ikegami Tsushinki Co., Ltd., both of Tokyo, Japan

[21] Appl. No.: 403,573

[22] Filed: Jul. 30, 1982

[30] Foreign Application Priority Data

Jul. 31, 1981 [JP] Japan ................................ 56-120164

[51] Int. Cl.[3] ............................................ H04M 7/18
[52] U.S. Cl. .................................. 358/106; 358/107; 356/237
[58] Field of Search ................. 358/106, 93, 126, 101, 358/107; 382/8; 356/237, 240; 250/562

[56] References Cited

U.S. PATENT DOCUMENTS 4,079,416  3/1978  Faani et al. ........................ 358/106
4,319,269  3/1982  Kajiura ............................... 358/106
4,376,951  3/1983  Miyazawa .......................... 358/106
4,403,294  9/1983  Hamada et al. .................... 358/106

Primary Examiner—John C. Martin
Assistant Examiner—Edward L. Coles
Attorney, Agent, or Firm—Fleit, Jacobson, Cohn & Price

[57] ABSTRACT

An automatic surface inspection system includes a surface scanner for scanning the inner surface of a paper cup rotated about its own axis and a preprocessing section receiving a picture element signal from the surface scanner for outputting a digital picture element signal to a reference axis setting circuit for detecting a reference axis in the sub-scanning direction. A first and a second discriminating circuit receives the digital picture element signal for conducting a surface inspection. The first circuit handles the main scanning direction while making necessary masking treatment in the main scanning direction and the second discriminating circuit handles the sub-scanning direction while making necessary masking treatment in the sub-scanning direction. A mask pattern circuit has a reference memory adapted to supply the discriminating circuit with pattern information. Thereafter, the respective discriminating circuits perform masking processing in real time on the basis of mask pattern information and corresponding portion from the reference memory so as to a total discriminating circuit decides whether or not the surface of said object inspected is acceptable or defective.

16 Claims, 56 Drawing Figures

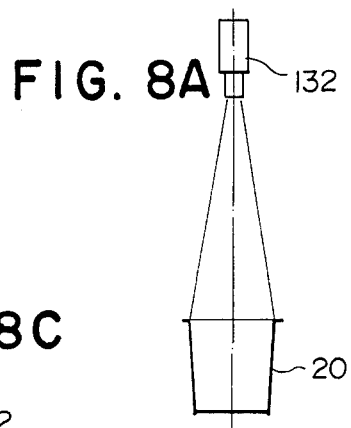
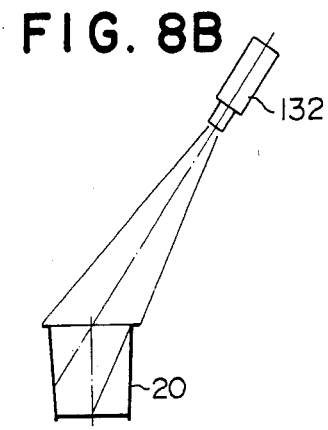
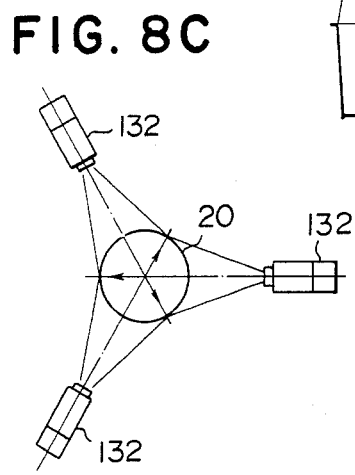
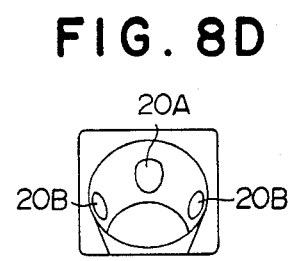
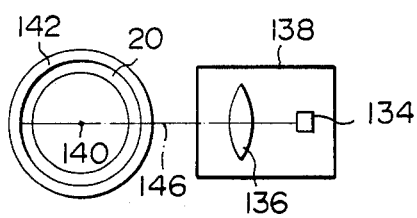
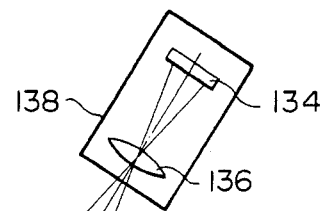
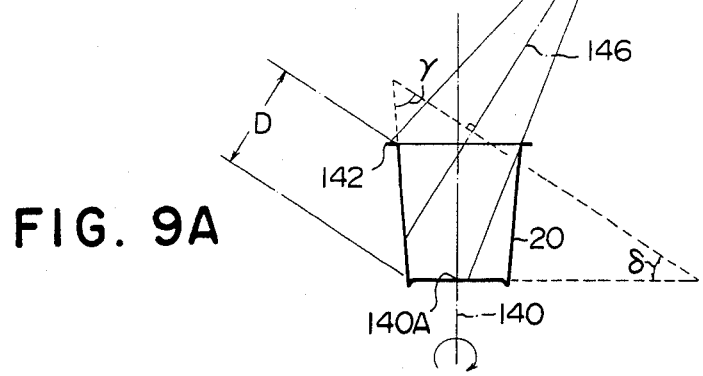

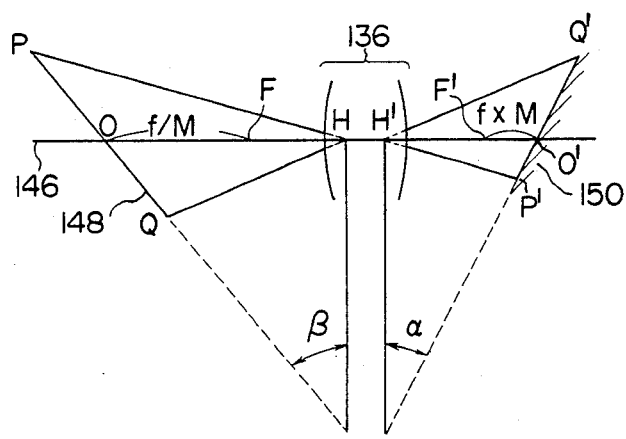
FIG. 10
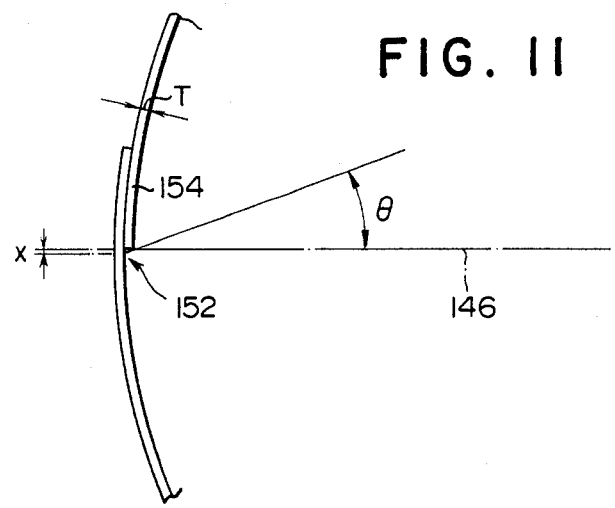
FIG. 11
FIG. 12A
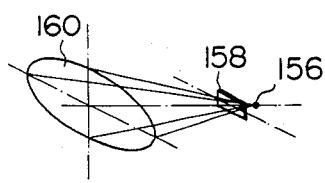
FIG. 12B
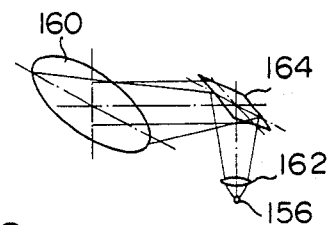
FIG. 12C
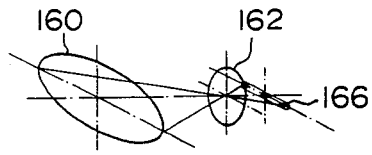

FIG.15A INPUTTED SIGNALS
FIG.15B SHAPED SIGNALS

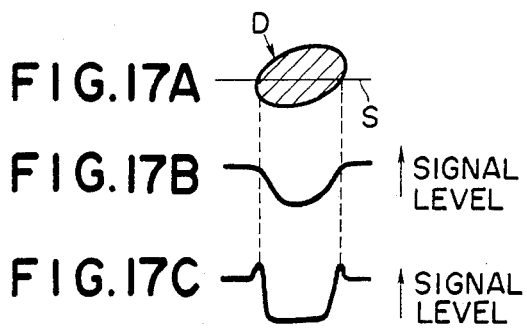

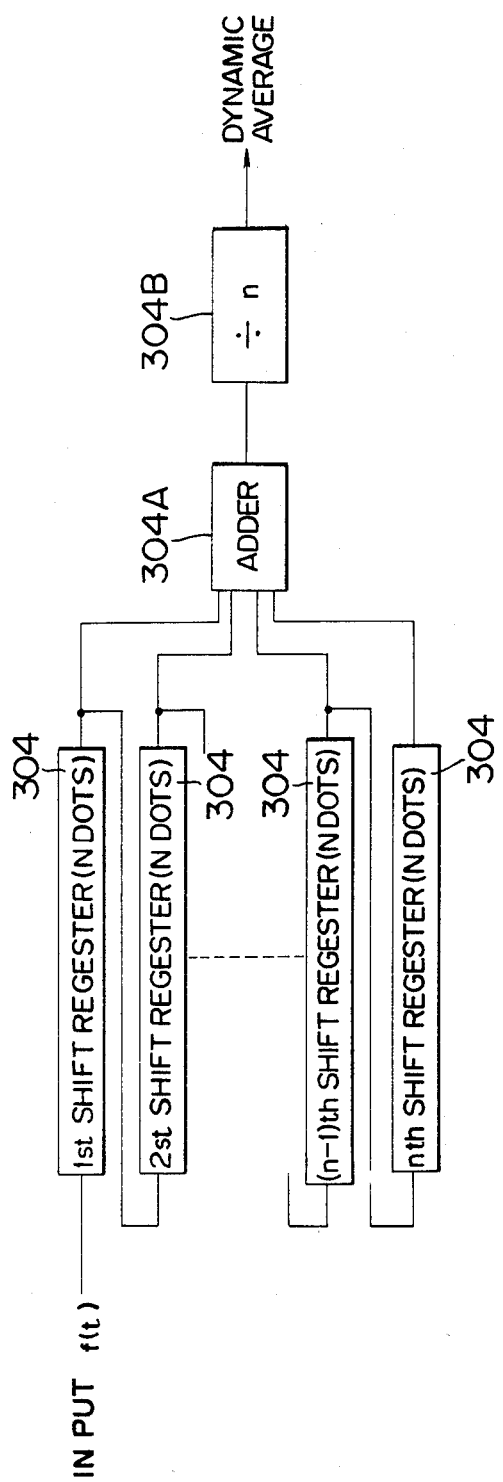

FIG. 27
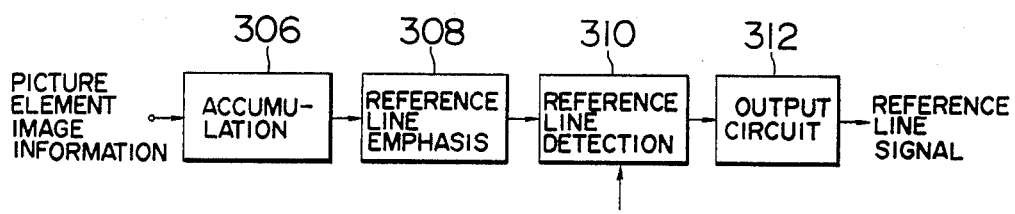
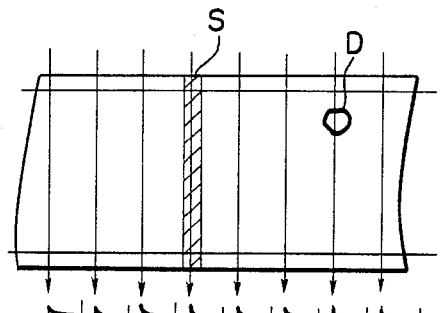
FIG. 28A
FIG. 28B
FIG. 28C

AUTOMATIC SURFACE INSPECTION SYSTEM

BACKGROUND OF THE INVENTION

This invention relates to an automatic surface inspection system, and more specifically, to such a system especially effective in automatically inspecting a surface for defects such as cracks and dirt.

Cup-shaped vessels such as paper cups are widely used not only as vessels in automatic vending machines but also as vessels for various kinds of foods. In these purposes of use, if the inner surface of such a vessel has a dead insect, hair, oil, etc. adhering thereto, it of course cannot be used as a vessel for foods. Further, even if the adhering material is harmless such as a chip of the vessel itself, the vessel will be apt to be rejected in use. Because of this, there is a very large need for inspection of the inner surface of cup-shaped vessels such as shaped paper cups, and therefore, the vessels have been visually inspected by humans in accordance with need. An experienced human inspector has good, flexible judgment and can comply with a very large number of inspection items with good accuracy in a reasonable inspection time. To the contrary, the accuracy of inspection by human inspectors varies greatly from individual to individual and depends greatly upon subjective factors and his mood or feeling at each occasion. In addition, a human inspector makes more errors as he becomes tired, and he cannot work continuously at a constant speed for a long time. Therefore, automation of such inspection has been desired. If an automatic inspection apparatus is used in place of the visual inspection by humans, it is possible to ensure a constant accuracy and objectivity in the result of inspection, and also, reduction of labor and continuous inspection over long periods are made possible.

However, in automatically inspecting cup-shaped vessels, there will be a problem in processing image information obtained from scanning of the surface of the cup-shaped vessels.

Recent developments in image processing technology have made it possible to detect and discriminate a very small defect on the surface of an object to be inspected. However, not only it is difficult to view the inner surface of a cup-shaped vessel such as a paper cup, but it is also necessary to detect very small defects, for example in the size of 0.1 mm. In addition, since it has been difficult to distinguish such extremely small defects from noise, it has been impossible to perform certain and reliable detection and discrimination. For the purpose of solving this problem, it is necessary not only to increase the resolving power of the surface scanning device such as a television camera, but also to effectively eliminate the noise and to emphasize minute defects so as to give a clear contrast between the defects and other portions. In addition, since the cup-shaped vessel has visible but non-defective portions such as a seamed portion, a printed mark and a convex-concave intentionally given, it is necessary to effectively separate information on these non-defective portions from surface image information of the cup-shaped vessel. Furthermore, when it is necessary to process a very large amount of image information as in the case of processing the image of the inner surface of the cup-shaped vessel, a computer has been ordinarily used heretofore. However, since the processing speed by computer greatly depends on the software in the computer, it can be generally said that if a computer compatible in cost with the surface inspection system is used for processing surface image information, the processing speed will not be fast. That is, use of a computer is not suitable for high speed processing.

Here, taking a paper cup as one example of a cup-shaped vessel, a detailed consideration shows that the paper cup ordinarily has an upper edge, a seam between the side and the bottom, a seam in the side, and also, in some cases, a straw hole formed in the bottom and covered by a peelable metal foil. These seams, edge and hole of the paper cup are detected when the paper cup is imaged. However, since these portions are not defects, they must be distinguished from defects. In such a case, it might be considered to use a deadband treatment, namely, a masking treatment on the surface information portion corresponding to non-defective portions such as seams and the like. In order to surely perform the masking treatment even if there is inaccuracy in position of the paper cup or displacement of the surface scanning device, the mask has to be enlarged to some extent to cover the non-defective portions. However, if this is so done, not only the portion to be masked but also real defective portions may be actually masked, so that the real defective portions cannot be detected. Such surface inspection is not sufficiently reliable. In other words, if there is a portion to be masked in the surface to be inspected, since there has heretofore inevitably been generated a portion which is not subjected to the defect detection because of the masking treatment, perfect defect detection has been impossible.

If a paper cup is positioned against the surface scanning device so that the seam in the side of the paper cup is directed along the main scanning direction of the surface detecting device, the upper edge and the side-bottom seam will be perpendicular to the main scanning direction. However, there has heretofore been no method which both can effectively mask a portion to be masked along the main scanning direction and another portion to be masked along the direction perpendicular to the main scanning direction, and can also perform the defect detection for the whole of the surface to be inspected so that there is no remaining portion not subjected to defect detection, thereby to completely detect any defect.

In addition, in order to perform selective masking of the image information obtained, a reference axis is necessary for collating a mask pattern with the image information obtained. But, if image scanning for surface inspection is started for the whole of a paper cup after there is detected what can be used as a reference axis in the surface of the paper cup, a long time is required for surface scanning of each paper cup. This is not suitable for high speed inspection.

OBJECTS

Accordingly, it is one object of this invention to provide an automatic surface inspection system having a scanning and processing apparatus which can image the surface of an object to be inspected and detect any minute visible defect with accuracy and at a high speed.

It is another object of this invention to provide an automatic surface inspection system having a scanning and processing apparatus which can perform a masking treatment in such a manner that there is no perfectly masked area, so that any visible defect can be surely detected.

It is a further object of this invention to provide an automatic surface inspection system which is simple in construction and can perform real-time processing and in which a mask pattern memory is sufficient if it has sufficient capacity to store only a mask pattern corresponding to a portion to be masked.

It is still another object of this invention to provide an automatic surface inspection system having a scanning and processing apparatus which effectively utilizes surface information obtained before a reference axis for a masking treatment is detected, so that the time for scanning the surface of a paper cup is minimized.

SUMMARY OF THE INVENTION

The above and the other objects of this invention are achieved by an automatic surface inspection system in accordance with this invention. This automatic surface inspection system comprises a surface scanning means for scanning the surface of an object to be inspected to output an analog picture element signal, and a processing device having a pre-processing section receiving said analog picture element signal from said surface scanning means for shaping said signal and converting it into a digital picture element signal, and a data processing section receiving said digital picture element signal from said pre-processing section for conducting surface inspection. Said data processing section includes a first reference axis setting circuit receiving said digital picture element signal from said pre-processing section for detecting a reference axis in the main scanning direction, a second reference axis setting circuit receiving said digital picture element signal from said pre-processing section for detecting a reference axis in the sub-scanning direction, a first detecting circuit having a first discriminating circuit receiving said digital picture element signal for conducting a surface inspection in the main scanning direction while making necessary masking treatment in the main scanning direction, a second detecting circuit having a second discriminating circuit receiving said digital picture element signal for conducting a surface inspection in the sub-scanning direction while making necessary masking treatment in the sub-scanning direction, and a mask pattern circuit having a reference memory adapted to supply pattern information on portions which should be excluded from surface inspection. Said first and second discriminating circuits are adapted to, after receiving said reference signal from said second reference axis setting circuit, perform masking processing in real time on the basis of mask pattern information of a corresponding portion from said reference memory so as to output inspection information. A total discriminating circuit receives the inspection information from each of said first and second discriminating circuits to decide whether or not the surface of said object inspected is acceptable or defective.

With the above arrangement, since defect detection is performed in each of the main scanning direction and the sub-scanning direction, any defect can be surely detected. Furthermore, if a seam is perpendicular to one of the two scanning directions, since the seam can be detected as a defect in the defect detection in the one scanning direction, it is necessary to mask the seam in the defect detection in the one scanning direction, but, since the seam is not detected as a defect in the defect detection in the other scanning direction, it is not necessary to mask the same in the defect detection in the other scanning direction. Therefore, since there is no portion masked in both the main scanning direction defect detection and the sub-scanning direction defect detection, by combining the defect detections in the two scanning directions, it is possible to make the perfectly masked portion substantially zero, so that there is no omission in the defect detection.

In one embodiment of the automatic surface inspection system in accordance with this invention, said second reference axis setting circuit is adapted to sum all digital picture element signals for each main scanning line, to obtain a dynamic average value on each sum value in the sub-scanning direction, to compare the dynamic average value with the sum value so as to seek the difference between the dynamic average value and the sum value, and to compare the difference with a predetermined value so as to determine, as the reference line, a scanning line of that sum value between which and the dynamic average value the difference is not less than said predetermined line. On the other hand, said first reference axis setting circuit is adapted to detect, as a reference line, the portion where the picture element signal firstly changes from the condition representing the dark to the condition representing the light after the start of each scanning.

In a preferred embodiment of the automatic surface inspection system in accordance with this invention, said pre-processing section has an outline-emphasizing and smoothening circuit which includes a first adder adapted to obtain the sum "g" of digital picture element signals of four picture elements adjacent vertically and horizontally to each picture element corresponding to each digital picture element signal "E", a second adder adapted to obtain the sum "$g_2$" of digital picture element signals of four picture elements adjacent in the upper-right, upper-left, lower-right and lower-left directions from said picture elements corresponding to said digital picture element signal "E", a first operational circuit receiving said sums "$g_1$" and "$g_2$" to output, as peripheral data "g", either the sum "$g_1$" or the average value $(g_1+g_2)/2$, a coefficient circuit supplying a weighting coefficient "K", a second operational circuit receiving said peripheral data "g", said weighting coefficient "K" and said digital picture element signal "E" for seeking an outline emphasizing signal $((K+4)E-g)/K$ and a smoothened signal $(KE+g)/(K+4')$ and an output selection circuit for selectively outputting either said outline emphasizing signal or said smoothened signal.

With the outline-emphasizing and smoothening circuit, even if a defect does not have sufficient contrast, since periphery of the defect can be emphasized in contrast to the other portions by using the outline-emphasizing signal, the defect can be easily detected. Alternatively, if much noise appears, the noise can be suppressed by using the smoothened signal.

In the preferred embodiment of the automatic surface inspection system in accordance with this invention, each of said first and second detecting circuits has a defect information pick-up circuit adapted to seek a dynamic average value on each inputted digital picture element signal in the scanning direction, to obtain a first difference signal between the dynamic average value and the inputted digital picture element signal, to compare said first difference signal with a first low threshold level so as to sense a defective portion of a relatively high concentration, to obtain a second dynamic average value on each of said difference signals, to compare said second dynamic average value with a second threshold level so as to sense an area where a defective portion of a relatively low concentration exists, to enlarge the extent of said area, and to compare a third low threshold level with said difference signal within said enlarged area so as to sense the defective portion of a relatively low concentration.

With this defect information picking-up circuit, either a dark defect or a light defect can be surely detected.

If a small portion to be masked exists behind and close to the sub-scanning direction reference axis, the detecting circuit is adapted to start its detecting operation with a time delay corresponding to the sub-scanning direction length of a mask pattern for the small portion from the start of scanning operation for the surface of the object to be inspected. With this operation, since the defect detecting circuit can always detect the above portion to be masked just after the sub-scanning direction reference axis is detected, a reference memory for storing a mask pattern corresponding to the above portion to be masked is sufficient if it has enough capacity to store only the mask pattern. In addition, it is possible to process in real time the surface image information corresponding to the above portion to be masked.

Also, in the preferred embodiment of the automatic surface inspection system in accordance with this invention, said processing device further includes an inspection information memory for storing the outputs from said first and second discriminating circuits until the reference axis signal is outputted from said second reference axis setting circuit, and a mask collating circuit for, after completion of the scanning operation for the surface of the object to be inspected, collating the inspection information in said inspection information memory with the corresponding mask pattern in said reference memory so as to output only inspection information on a portion which should not be masked. In this case, said total discriminating circuit is adapted to receive the inspection information from said first and second discriminating circuits and said mask collating circuit. With this arrangement, it becomes unnecessary to scan the whole of the surface of an object to be inspected after detection of the reference axis, so that the time necessary for scanning the surface can be shortened and the inspection speed can be made fast. In this embodiment, if the inspection information in said inspection information memory is collated with the corresponding mask pattern in said reference memory in the order of high address number to low address number, the processing circuit construction can be made simple.

The above and the other objects and effects will become apparent from the following detailed description, with reference to the accompanying drawings, of an automatic surface inspection system for inspecting the inner surface of paper cups, which embodies this invention. But, it should be noted that the automatic surface inspection system in accordance with this invention is useful not only for the inner surface inspection of paper cups but also for inspection of the surface of anything which has a relatively large surface.

BRIEF DESCRIPTION OF THE DRAWINGS

FIG. 8A shows the location of a paper cup and an image pick-up device when the paper cup is imaged from a position directly above the cup;

FIG. 8B shows the location of a paper cup and an image pick-up device when the paper cup is imaged from a position obliquely above the cup;

FIG. 8C shows the location of a paper cup and three image pick-up devices when the paper cup is imaged from three positions which are apart from each other by the same angular intervals and are oblique and above the cup;

FIG. 8D illustrates the image obtained when a paper cup is imaged from a position obliquely above the cup;

FIG. 9A is a diagrammatic vertical sectional view showing the positional relation between a paper cup and an image pick-up device and an optical axis of the image pick-up device when the paper cup is imaged from obliquely above the cup;

FIG. 9B is a diagrammatic top view of the location as shown in FIG. 9A;

FIG. 10 illustrates the relation between a surface to be inspected inclined against the optical axis of the image pick-up device and the image surface of the surface to be inspected;

FIG. 11 illustrates the method of illumination for producing the shadow of a seam of a paper cup;

FIGS. 12A, 12B and 12C diagrammatically show methods of illuminating a surface to be inspected of a paper cup;

FIGS. 15A and 15B are graphs showing a variation in level over one scanning of an analog picture element signal obtained from the image pick-up device and the signal shaped by a waveform shaping circuit, respectively;

FIGS. 17A, 17B and 17C illustrate the advantage of the outline emphasizing treatment;

FIG. 18 shows the positional relation of picture elements sampled for the outline emphasizing treatment and a smoothening treatment;

FIGS. 19A and 19B illustrate the advantage of the smoothening treatment;

FIGS. 21A and 21B are waveform diagrams showing the effect of a dynamic average;

FIGS. 22A and 22B are waveform diagrams showing the relation between the picture element signal subjected to the dynamic average treatment and a threshold level for detecting a dark defect, and the defect signal detected, respectively;

FIGS. 23A to 23F are waveform diagrams showing the steps of the signal processing for detecting a light defect;

FIG. 26 is a block diagram of a shift register array used in a detecting axis converting circuit;

FIG. 27 is a block diagram of a reference line detecting circuit;

FIGS. 28A, 28B and 28C are a developed view of the side surface of the paper cup and waveform diagrams which show the steps of the signal processing for detecting the side seam of the paper cup;

DETAILED DESCRIPTION OF THE PREFERRED EMBODIMENTS

Figure 1:
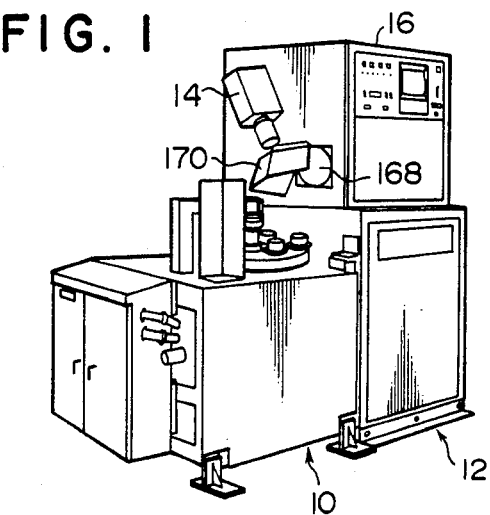
FIG. 1 is a diagrammatic perspective view of an automatic surface inspection system for paper cups constructed in accordance with this invention.

Referring to FIG. 1, there is shown an automatic surface inspection system in accordance with this invention adapted to inspect the inner surface of paper cup. This surface inspection system comprises a conveying apparatus 10 for receiving paper cups to be inspected, feeding them to an inspection position and rotating each paper cup about its own axis at the inspection position, and a scanning and processing apparatus 12 for scanning the inner surface of each paper cup and processing the obtained information so as to discriminate whether the cup inspected is defective or non-defective. The scanning and processing apparatus 12 has a surface scanning device 14 for scanning the inner surface of each paper cup positioned in the inspection position, and a processing and discriminating device 16 for processing the surface information obtained by the surface detecting device 12 so as to discriminate whether or not there is even a minute defect.

Figure 2:
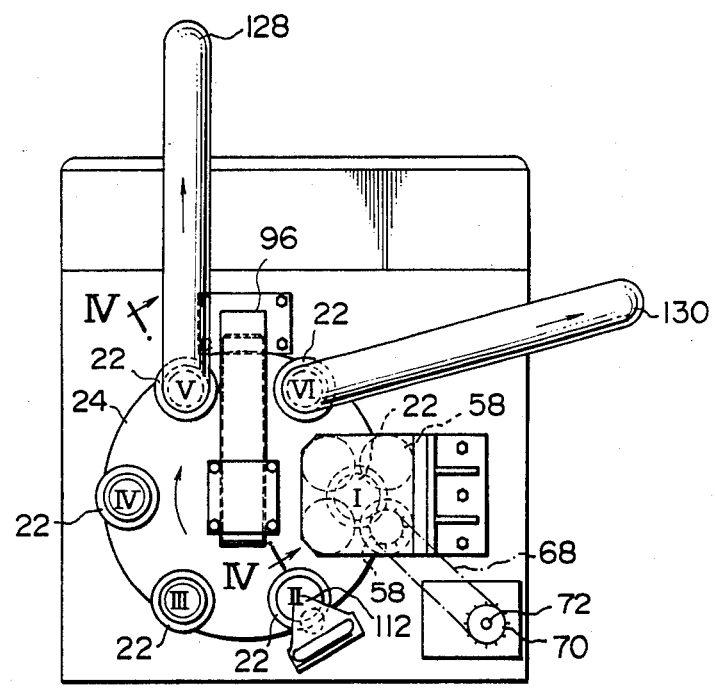
FIG. 2 is a top view of a conveying apparatus used in the system shown in FIG. 1.
Figure 3:
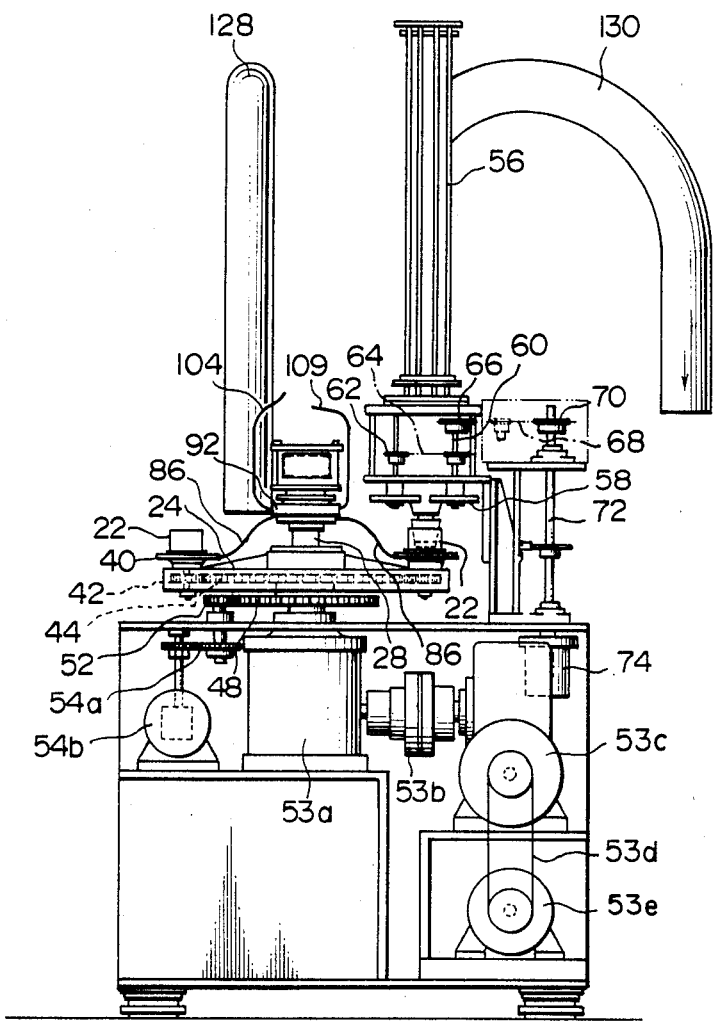
FIG. 3 is a partially omitted front view of the conveying apparatus shown in FIG. 2.
Figure 4:
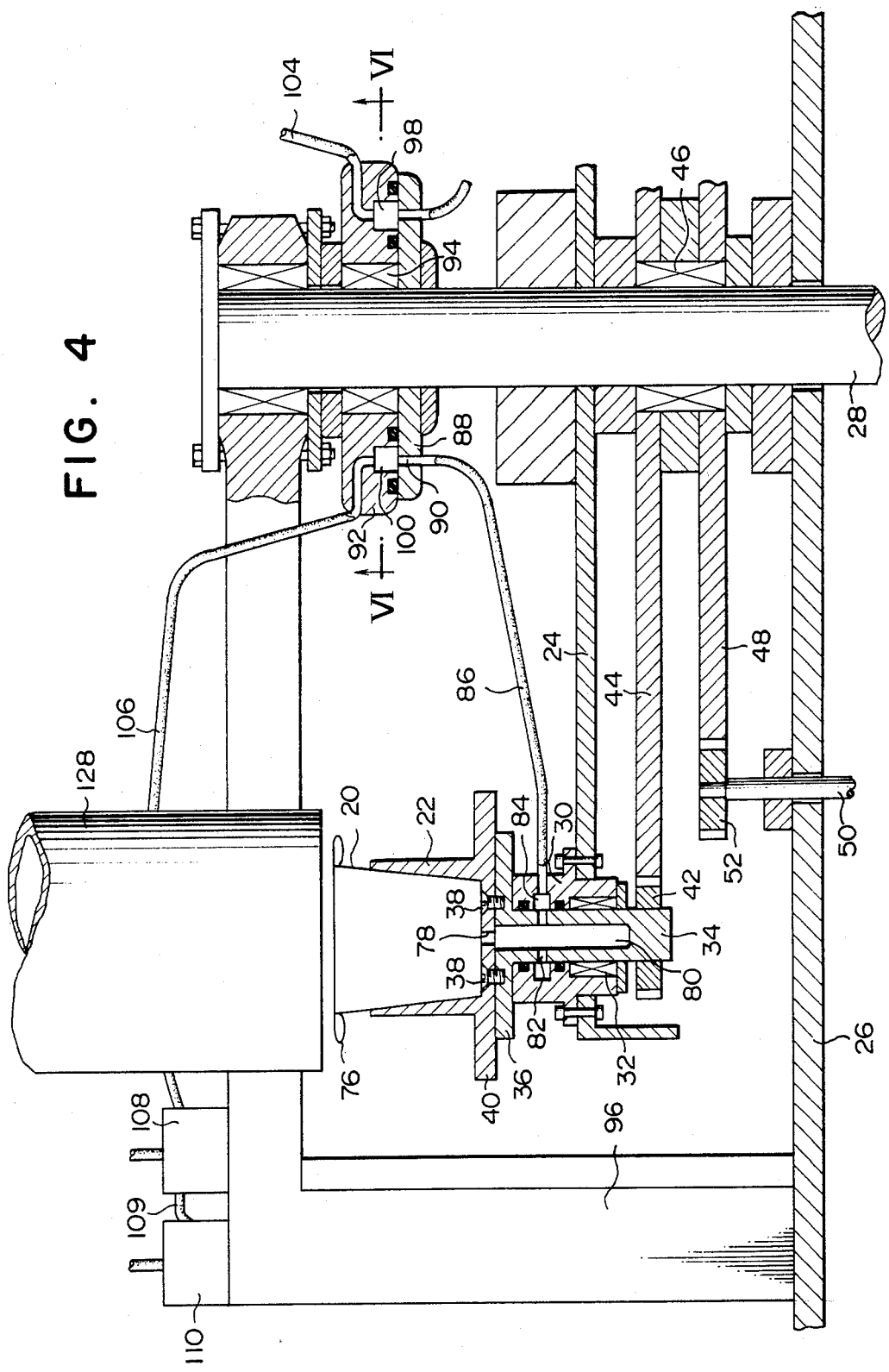
FIG. 4 is a partial sectional view taken along the line IV—IV in FIG. 2.

Next referring to FIGS. 2 to 4, there is shown the conveying apparatus 10. FIG. 2 is a top view of the conveying apparatus 10; FIG. 3 is partially broken front view of the conveying apparatus; and FIG. 4 is a partial sectional view take along the line IV—IV in FIG. 2.

As seen from FIGS. 3 and 4, the conveying apparatus 10 comprises a plurality of cup holders 22 having a concave portion whose inner configuration and dimensions are substantially the same as the outer configuration and dimensions of a lower portion of a paper cup 20. Each of the cup holders 22 has a depth sufficient to snugly hold the paper cup without allowing positional displacement of the paper cup, and preferably has a depth sufficient to receive at least a lower half portion of the paper cup. If the paper cup is snugly held by the cup holder 22, the paper cup can be rotated by rotating the cup holder 22. In addition, since the concave portion of the cup holder 22 is substantially the same in shape and dimensions as the outer configuration of the paper cup, the center axis of the cup holder can be easily and accurately aligned with the center axis of the paper cup, and therefore, the paper cup can be rotated about its own center axis by rotating the cup holder about its own axis.

As is apparent from FIG. 2, for example, six cup holders 22 are located on a peripheral portion of an indexing table 24 at equal angular intervals. This indexing table 24 is fixed to a rotating shaft 28 which is in turn rotatably supported by a frame 26 of the conveying apparatus 10. The indexing table 24 has six boss members 30 arranged on the peripheral portion of the table 24 at equal angular intervals of 60 degrees and fixed to the table 24 by suitable fastening members such as bolts-and-nuts. Each of the boss members 30 rotatably supports a rotating shaft 34 through a bearing member 32. The rotating shaft 34 has a flange 36 formed on an upper end thereof, to which one cup holder 22 is fixed by screws 38. Therefore, the cup holder can be exchanged in accordance with the size and the configuration of the paper cup to be inspected. In addition, by rotating the cup holder 22 in the boss member 30, the cup holder can be rotated about its own axis at the periphery of the indexing table 24.

As seen from FIG. 2, the conveying apparatus 10 comprises a paper cup supplying station I, a pushing station II where a paper cup supplying to the cup holder is surely pushed in the cup holder, an inspection station III, a spare station IV, a defective product ejecting station V and a good product feed-out station VI. Since a linear image sensor array is used as a scanning device in the inspection station as described in detail hereinafter, it is necessary to stop the rotation of the indexing table 24 when the paper cup to be inspected reaches the inspection station III, and then to rotate the cup holder 22 about its own axis in the inspection station III. In other words, it is necessary to intermittently rotate the indexing table and to rotate the cup holder about its own axis when the indexing table is stopped. For high speed inspection, it is also necessary to make the time from the start of the rotation of the cup holder 22 in the inspection station to the constant speed rotation of the cup holder, as short as possible. One possible way for this is to give rotation to the cup holder beforehand in the station before the inspection station. As one way for achieving this, it is possible to provide a friction wheel adapted to friction-contact with the periphery of a flange 40 of the cup holder 22, in each of the inspection stations and the station before the inspection station. But, this way would not be suitable because a complicated mechanism would be necessary and frequent replacement of the friction wheel would be necessary.

Figure 5:
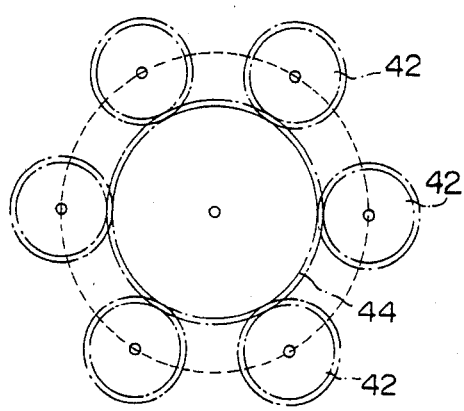
FIG. 5 is an illustrative view showing the relation between a sun gear and planetary gears used in the conveying apparatus shown in FIG. 2.

In view of this, in this embodiment, the conveying apparatus has a sun-and-planet gear mechanism in which each of the cup holders 22 has a planetary gear 42 in mesh with a sun gear 44 in a positioned location as shown in FIG. 5. Specifically, the planetary gear 42 is fixed to the lower end of the rotating shaft 34, and the sun gear 44 in mesh with the planetary gears is rotatably mounted on the shaft 28 through a bearing member 46. A gear 48 rotatable with the sun gear 44 is also rotatably supported on the shaft through the bearing member 46. With this arrangement, the sun gear 44 and the gear 48 are rotatable in relation to the rotating shaft 28 namely, independent of the shaft 28. The gear 48 is meshed with a gear 52 fixed to a rotating shaft 50 which is in turn rotatably supported by the frame 26. Therefore, rotation of the shaft 50 causes rotation of the sun gear 44 independently of the shaft 28 through the gears 52 and 48, ultimately rotating the cup holder about its own axis through the gear 42.

With this arrangement, if the sun gear 44 is rotated at a constant speed, the planetary gear 42 and hence the cup holder 22 are rotated about their own axes at a constant speed not only during the rotation period of the indexing table 24 but also during the stationary or rest interval of the same table. If the rotational direction and the angular speed of the indexing table 24 in the rotating condition are the same as those of the sun gear 44, when the indexing the table is in an angularly moving condition, the planetary gear 42 and hence the cup holder 22 are stationary against the indexing table 24, but still rotate about their own axes at a constant speed. When the indexing table 24 is stopped in a rest period of its intermittent rotation, the cup holder 22 continuously rotates about its own axis at the same constant speed. Therefore, an accelerating time for the rotation of the cup holder about its own axis in the inspection station is not necessary, so that high speed inspection becomes possible.

In this embodiment, it is necessary to rotate the cup holder at least one revolution during each rest period of the indexing table. For this purpose, it would be ordinarily thought of to establish a constant relation between the rotation of the indexing table and the rotation of the cup holder about its own axis. As one means for this purpose, the rotating shafts 28 and 50 can be driven by the same motor respectively through respective gear mechanisms having suitable reduction ratio, so that the cup holder is always rotated one revolution during the rest period of the indexing table. This way is very convenient because only one motor is sufficient and the interrelation in movement between the indexing table and the cup holder can be determined by selecting their reduction ratio.

Taking into consideration adjustment for sensitivity of the scanning and processing apparatus and other maintenance work, it is preferred that only the cup holders be rotatable at the same speed as that of the holder in the actual inspection operation, while maintaining the indexing table in a stationary condition.

In the disclosed embodiment, therefore, the rotating shaft 28 is coupled through a cam type indexing mechanism 53a for producing intermittent rotation, a coupling shaft 53b, a reduction mechanism 53c of a reduction ratio variable type, and a belt 53d to an AC motor 53e. On the other hand, the rotating shaft 50 is coupled through a reduction mechanism 54a to a DC motor 54b for continuous rotation. But, it may be constructed such that the same motor is coupled through a gear mechanism to the rotating sahft 50 and through another gear mechanism and a clutch device to the rotating shaft 28 so that only the cup holders are continuously rotated around their own axes while intermittently rotating the indexing table by disengaging and engaging the clutch.

A paper cup stacking tower 56 is located above the supplying station. Below the tower 56 there is a power cup supplying mechanism comprising four cup supplying screws 58 each of which is fixed to a rotatable shaft 60 having a sprocket 62 connected through a chain 64 to the sprocket 62 associated with the other screws 58, so that the four screws 58 are rotated in synchronism. One of the four shafts 60 is adapted to be driven through a sprocket 66, a chain 68, a sprocket 70 and a shaft 72 by a motor 74 which is controlled to rotate in synchronism with the indexing table 24. When the motor 74 is energized to rotate the shaft 72, the four cup supplying screws 58 are rotated in synchronism, so that an upper flange (as indicated by Reference Numeral 76 in FIG. 4) of the lowermost paper cup in the tower 56 is caught in a valley of each screw 58 and is separated from the other cups in the tower 56 in accordance with the rotation of each screw 58 so as to be supplied into a cup holder that stays in the supplying station I.

Figure 6:
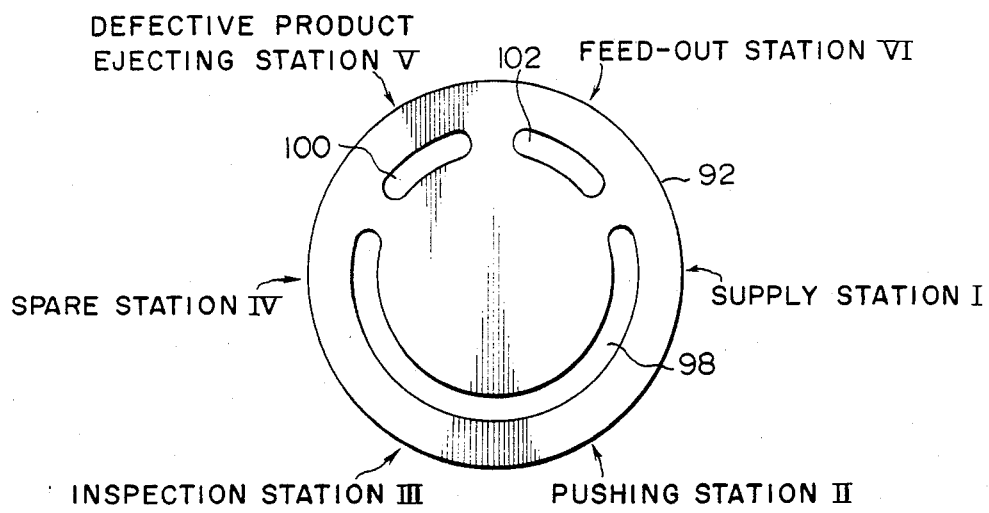
FIG. 6 is a sectional view taken along the line VI—VI in FIG. 4.

In order to surely receive and hold in the cup holder the paper cup that has been supplied thereto by the cup supplying screws 58, the supplied cup is vacuum-sucked by the cup holder 22 in the shown embodiment. For this purpose, the cup holder 22 has a hole 78 formed in the bottom thereof and brought into communication with an axial hole 80 formed in a center axis portion of the rotating shaft 34. This shaft 34 also has radial holes 82 extending from the outer side surface of the shaft to the center axial hole 80. The boss member 30 has an annular inner channel 84 formed in the inside surface thereof to surround the radial holes 82. This channel 84 is connected to one end of a hose 86, which is in turn connected at the other end thereof to one of six holes 90 formed at the same angular intervals of 60 degrees in a peripharal portion of an annular member 88 fixed to the rotating shaft 28. This shaft 28 has another annular member 92 rotatably mounted thereon by a bearing member 94 and formed with three arched grooves 98, 100 and 102 in the surface thereof facing the holes 90 as shown in FIG. 6 to communicate with the holes 90, respectively. The annular member 92 is fixed to a tip end of a horizontal arm portion of an arm 96 secured to the frame 26.

As seen from FIG. 6, the groove 98 of the annular member 92 extends in the circumferential direction to form a vacuum chamber in a portion of the annular member corresponding to the supplying station I, the pushing station II, the spare station III and the inspection station IV. The groove 100 extends to form a first high pressure chamber in a portion corresponding to the defective product ejecting station V, and the groove 102 forms a second high pressure chamber in a portion corresponding to the non-defective product feed-out station VI. The vacuum chamber 98 is connected through a hole 104 to a vacuum source (not shown). The first high pressure chamber 100 is connected through a hose 106 and a solenoid operated valve 108 to a compressed air source (not shown) and the second high pressure chamber 102 is connected through a hose 109 and a solenoid operated valve 110 to a compressed air source (not shown).

With this arrangement, even if the shaft 34 is continuously rotated about its own axis, the hole 80 of each shaft 34 is ceaselessly in communication through the holes 82 with the annular channel 84 of the associated boss member 30, and each of the holes 90 of the annular member 88 in communication with the associated channel 84 through the hose 86 will communicate with one of the vacuum chamber 98 and the first and second high pressure chambers 100 and 102. Specifically, while the cup holder is positioned between the supplying station I and the inspection station IV inclusive, a negative pressure is produced in that cup holder through the hole 78. Therefore, when one paper cup is supplied to one cup holder staying in the supplying station I by the cup supplying screws 58, the supplied cup is sucked into the cup holder and firmly received and held by the cup holder. The paper cup continues to be held by the cup holder until that cup holder reaches the defective product ejecting station.

The paper cup received by the cup holder in the above mentioned manner is forcedly pushed into the cup holder by a pushing mechanism 112 in the pushing station II, in the case of the disclosed embodiment. This operation is effective when the paper cup supplied into the cup holder in the supplying station is not fitted into the cup holder in place, because the paper cup is forcedly positioned in place in the holder in contact with the inner surface of the holder in a proper positional relation by pushing the cup into the cup holder. Therefore, if the paper cup can always be fitted into the cup holder in place by only the vacuum suction in the supplying station I, the pushing mechanism is not necessary. To the contrary, it may be constructed such that the vacuum sucking mechanism is omitted so that the paper cup is merely dropped into the cup holder in the supplying station, and the paper cup dropped into the holder is pushed to fit into the holder in place in the pushing station.

Figure 7:
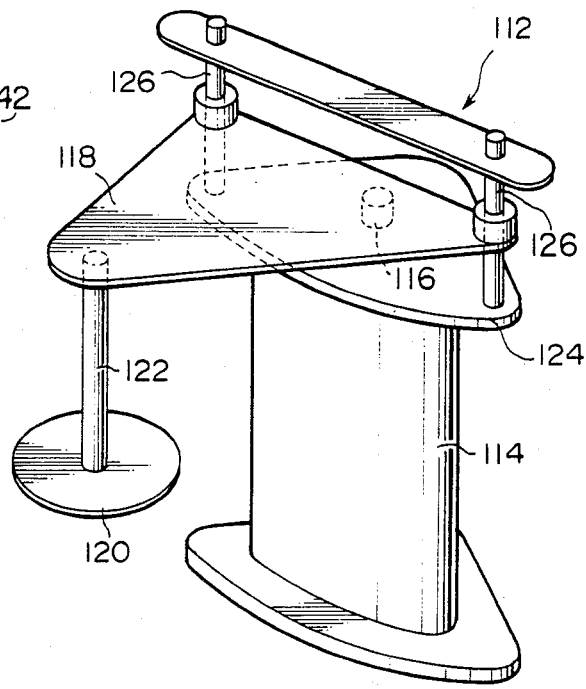
FIG. 7 is a perspective view of a paper cup pushing mechanism used in the conveying apparatus in FIG. 2.

As seen from FIG. 7, the pushing mechanism 112 comprises a casing 114 accommodating a piston-cylinder device whose piston rod 116 provided at its top end with a triangular plate 118. To one corner of the triangular plate 118 there is secured an upper end of a shaft 120 which has a pushing plate 120 fixed to a lower end thereof. The two remaining corners of the plate 118 are slidably supported by a pair of guide shafts 126 fixed to an upper flange 124 of the casing 114. By operating the piston-cylinder device in the casing 114, the pushing plate 120 is moved upwardly and downwardly to surely push the paper cup to the bottom of the cup holder, so that the cup is fitted and held in the holder in place.

The paper cup forcedly fitted into the cup holder in the pushing station is fed to the inspection station III where it is inspected, and thereafter is fed through the spare station IV to the defective product ejecting station V. If the paper cup has been found to be defective by the inspection performed by the inspection station, that paper cup is ejected from the cup holder 22 to a defective product exhausting duct 128 in the ejecting station V by opening the solenoid operated valve 108 so as to supply compressed air to the bottom of the holder 22 through the first high pressure chamber 100. To the contrary, if the paper cup has been found to be non-defective, that cup is not ejected in the ejecting station V and is fed through the ejecting station V to the feed-out station VI. On the other hand, the solenoid operated valve 110 is energized to be opened at every rest period of the indexing table, so as to supply compressed air to the bottom of the cup holder 82 through the second high pressure chamber 102. Therefore, the paper cup fed to the feed-out station is ejected from the cup holder and fed through a feed-out duct 130.

In order to scan the inner surface of a paper cup that is positioned in the inspection station by the aforementioned conveying apparatus and is rotated about its own axis, there is provided the surface scanning device 14. As a surface scanning method, the following three typical methods would come to mind. Namely, a first method of using an industrial television camera; a second method of sweeping the surface to be inspected with a laser beam and detecting the reflected light by a photosensor; and a third method using a line image sensor constituted of solid state image pick-up elements.

If an industrial television camera is used for scanning the surface to be inspected, the whole of the surface can be image-picked up at once. In addition, since this method can be realized by using a conventional television camera as it is, it is not expensive. However, since the conventional television camera ordinarily uses an image pick-up tube such as a vidicon, there is a problem of lag comparable to the after image in the human eye. Namely, if the paper cup is continuously moved, the image obtained from the television camera directed to the paper cup is blurred somewhat, resulting in a decrease in resolving power, whereby it becomes impossible to detect a very small defect. In order to overcome this problem of lag, it is, for example, necessary to illuminate the surface by an intantaneous light emitting means such as a xenon flash lamp so as to obtain a substantially still image, or to use an indexing conveying apparatus capable of keeping the surface to be inspected in a stationary condition in the inspection station.

Even if one of these two ways is adopted, if the paper cup is viewed by a camera tube 132 from vertically above the center of the paper cup 20 as shown in FIG. 8A, the bottom of the cup is seen from the front, but the side surface of the cup is inclined to the optical axis of the camera 132 at a small angle. Therefore, the image of the bottom will have sufficient resolution, but the image of the side surface cannot have sufficient resolution so that the capacity of defect detection to the side surface will be much smaller than that for the bottom.

This problem can be solved by locating the camera 132 obliquely above the center of the paper cup 20 so that the angle between the side surface of the cup and the optical axis of the camera is made larger so as to increase the defect detecting capacity for the side surface as shown in FIG. 8B. In this case, however, the whole of the inner surface of the paper cup cannot be imaged by only one camera.

Therefore, it can be thought of to locate at least three cameras 132 obliquely above the center of the paper cup 20 and at equal angular intervals as shown in FIG. 8C. With this arrangement, the defect detection capacity can be increased, but, since at least three different image signals are obtained by at least three cameras, respectively, at least three signal processing systems of the same construction are necessary, resulting in a large-scale system. Particularly, since it is expected to be necessary to process signals for detection of an upper edge, a seam in the side surface, and a seam between the side and the bottom of a paper cup, and since any defect should be detected without regard to concentration of the defect, a signal processing system will be required to have a large processing capacity and a high performance. Such a system with be inevitably complicated, large-scale and very expensive. Therefore, it can be easily expected that use of at least three of such systems will make the cost of the overall surface inspection system extremely high.

In addition, when the paper cup is imaged by the camera positioned obliquely above the cup, as apparent from FIG. 8D the angle between the optical axis of the camera and the side portion is decreased from a portion 20A at the center of the viewing field of the camera to portions 20B at the periphery of the viewing field. Therefore, the defect detection capacity is decreased from the portion 20A to the portions 20B. In other words, the detection capacity is not even over the whole of the inner surface of the cup viewed by the camera.

In the laser type surface scanning method, for example, in a flying spot method, it can be conceived to have a thin laser beam sweep to vertically move on the inner surface of a paper cup that is being rotated about its own axis, so that the whole of the inner surface is ultimately scanned. Presence of defects can be discriminated on the basis of the level of reflected light from the inner surface. In this method, it is necessary to rotate the paper cup about its own axis, but it is sufficient to provide only one signal processing. In addition, there is no unevenness in defect detection capacity in the rotational direction of the cup. Therefore, this method can be said to be advantageous over the method of using the industrial television camera.

However, the method of using the laser beam is disadvantageous in the following points. Firstly, in order to make the laser beam sweep, there are required, for example, swinging mechanisms such as a swinging mirror or a rotating mirror. However, these mechanisms have problems in adjustment and life. Secondly, since a laser beam is a monocolor light, it is impossible to detect any color of defects. Thirdly, laser light generating devices are ordinarily short in life. Fourthly, since it is difficult to accurately determine correspondence between the signals obtained and the positions on the inner surface of the paper cup, it is also difficult to perform data processing utilizing the positional relation among picture elements.

Next, a linear image sensor array constituted of solid state image sensing elements such as a charge-coupled image sensing device and a bucket-brigade image sensing device will be reviewed. If such a linear solid state image sensor array is located along the scanning direction of the laser beam as mentioned above, (1) the moving mechanism can be completely removed from the optical system; (2) all portions other than an illuminating means can be constructed by solid state elements, so that the system has a long life and stable performance over a long time; (3) since the image sensor is sensitive over a very large range of wavelengths, it is possible to detect any visible defect regardless of color; and (4) since the positional relation among picture elements is clear, it is possible to accurately perform masking of image information corresponding to the seams of a paper cup and the like, and therefore, it is also possible to make the mask small.

In view of the above, a linear solid state image sensor array is used in the surface scanning device 14 of the disclosed embodiment.

In order to scan the whole of the inner surface of a paper cup while the cup is rotated one revolution about its own axis, as shown in FIG. 9A, a camera 138 including a linear solid state image sensor array 134 and an object lens 136 is located to view the paper cup 20 at the inspection station from a position obliquely above the cup so as to put within its visual field the point 140A of the cup bottom through which the rotating axis 140 of the cup passes and an upper edge portion 142 of the cup remote from the camera. In addition, the linear image sensor array 134 in the camera 138 is positioned such that the plane including a longitudinal axis of the sensor array 134 and the rotating axis 140 of the cup 20 perpendicularly intersects the side surface, as shown in FIG. 9B. With this arrangement, while the paper cup is rotated about its own axis, the whole of the inner surface of the cup is scanned by the linear image sensor array 134.

Assume that the angle between the side surface being inspected and the plane perpendicular to the optical axis 146 of the camera is represented by $\gamma$, and the angle between the bottom surface and the same plane perpendicular to the optical axis 146 is represented by $\delta$. The resolutions for the side surface and the bottom surface are expressed by $R \cos \gamma$ and $R \cos \delta$, respectively where R is the resolution when the surface to be scanned is perpendicular to the optical axis of the camera. Therefore, the camera can be located to fulfill the relation of $\gamma = \delta$ so that the resolution for the side surface of the paper cup will be substantially equal to that for the cup bottom surface. However, the side and bottom surfaces of the cup rotating about its own axis are scanned in the axial direction of the cup, the scanning line density in the bottom surface is greater than that in the side surface. Therefore, in order to make the defect detection capacity for the side surface of the cup substantially equal to that for the cup bottom surface, it is preferably located so that the angle $\gamma$ is greater than the angle $\delta$ to some extent.

In any case, since the angle between the side surface and the bottom surface is a right angle or an angle slightly greater than the right angle, when the paper cup is viewed by the linear sensor array from a position obliquely above the cup, the angles $\gamma$ and $\delta$ will be around 45 degrees. Therefore, the resolution will inevitably be lower than when the surface to be inspected is perpendicular to the optical axis 146 of the camera. In order to compensate for the decrease in resolution, the number of the image sensing elements in the linear sensor array is increased. For example, to obtain substantially the same resolution as that obtained when the surface to be inspected is perpendicular to the optical axis of the camera, the linear sensor array is required to have image sensing elements of the number obtained by multifying by the square root of two the number of the image sensing elements in the linear sensor array used when the surface to be inspected is perpendicular to the optical axis.

Here, reviewing the surface image obtained by the linear image sensor array, resolution in the scanning direction is determined by the number of the elements in the linear sensor array, and resolution in the sub-scanning direction is determined by the rotational speed of the paper cup and the scanning cycle of the linear sensor array. In the disclosed embodiment, when the paper cup was rotated about its own axis at one revolution per 0.25 seconds, and a linear sensor array consisting of 1024 elements was scanned at the main scanning frequency of 5.5 KHz, the resolutions in the main scanning and sub-scanning directions were 0.1 mm per bit and 0.3 mm per bit, respectively, in the case of an ordinary size paper cup. The frequency of the image formation obtained at that time was about 6 MHz, and the image information was outputted at the speed of about 167 nanoseconds per bit. Information outputted at such a speed is sufficiently processible.

As mentioned above, the side surface and the bottom surface of a paper cup to be inspected are inclined to the optical axis of the camera. In order to produce an image of such inclined surfaces on the linear sensor array without blur, it is necessary to have the depth of field D as shown in FIG. 9A. This required depth of field depends upon the depth of the paper cup to be inspected and the angle between the inner surface of the cup and the optical axis of the camera, but, in any case, it is necessary to have a considerable depth of field. On the other hand, the depth of field depends upon the distance between the camera and the cup to be inspected, the focal distance of the object lens and the lens opening. To obtain a deep depth of field, it is necessary to use an object lens having a long focal distance and to make the aperture as small as possible. However, in order to obtain a deep depth of field by the stopping down the aperture, the aperture has to be made like the pinhole of a pinhole camera. If this is so done, the amount of light necessary for illuminating the cup to be inspected will become very large. This is not practical. To the contrary, if an ordinary size of paper cup is imaged from obliquely above the cup with an ordinary lens opening, a necessary depth of field will be ±40 mm. But, since the camera has to be located within a distance of not greater than 1 m from the cup to be inspected, it is not possible to use an object lens which has a sufficiently long focal distance to give such a deep depth of field, for example, a lens having a focal distance of several meters. Therefore, the problem of the depth of field cannot be solved by selection of the lens opening.

Rather, for the purpose of suppressing the amount of light for illuminating the cup to be inspected, the aperture is preferably made as large as possible. In view of this and in order to obtain a sufficient depth of field at a relatively large lens opening, as shown in FIG. 10, a photosensitive surface 150 of the linear sensor array is inclined to the optical axis 146 in a direction opposite to the inclining direction of the surface 148 to be inspected against the object lens 136. Now, assume that the lens 136 has a focal distance of "f". In order to obtain the magnification of "M" on the optical axis 146, the intersecting point "O" between the optical axis 146 and the surface 148 to be inspected is located at a position forwardly apart from a front principal point "H" by the distance f+f/M, and the image point "O'" on the optical axis 146 is located at a position backwardly apart from a rear principal point "H'" by the distance f+(f×M). The photosensitive surface 150 is located to pass through the image point "O'". With this arrangement, if the angle between the surface 148 to be inspected and the front principal surface of the lens 136 is β, the photosensitive surface 150 is inclined to the optical axis 146 so that the angle α between the photsensitive surface 150 and the rear principal surface of the lens 136 meets the relation of tan α=M tan β. In this construction, the image of the inclined surface 148 is sharply produced on the inclined photosensitive surface 150 without blur.

In this case, the image of the point "p" on the surface 148 to be inspected most remote from the lens 136 is formed on the point "p'" on the photosensitive surface 150, and the magnification of the image of the point "P" is expressed by $$\frac{M}{1+\frac{M}{f} \times PO \sin \beta}$$

The image of the point "Q" on the surface 148 to be inspected nearest to the lens 136 is formed on the point "Q'" on the photosensitive surface 150, and the magnification of the image of the point 37 Q" is expressed by $$\frac{M}{1-\frac{M}{f} \times OQ \sin \beta}$$

As seen from the above, the magnification varies from position to position on the surface to be inspected, and this results in distortion in the image obtained. But, this does not become a problem in defect detection because it is sufficient if it is possible to detect whether or not defects such as cracks and dirt exist on the inner surface and it is not necessary to accurately determine the size of the cracks and dirt. Therefore, if the presence of defects can be detected, slight difference in magnification is not any problem. If one wishes to solve this problem of magnification, the density of the image sensing elements on the photosensitive surface 150 may be gradually increased from the point Q' to the point p'.

In the actual inspection of paper cups, either the side surface or the bottom surface of the paper cup may be put on the surface 148 to be inspected. However, the surface having a longer length in the scanning direction is preferably put on the surface 148 to be inspected. On the other hand, either the side surface or the bottom surface of the paper cup is positioned apart from the surface 148 to be inspected as shown in FIG. 10. But, this is not a substantial problem in the surface inspection of the cup inner surface.

In the aforementioned manner, the inner surface can be imaged without blur. In order to detect what can be regarded as defects by a human inspector, by a linear image sensor array, it is preferred that the linear image sensor array being used has the same spectral sensitivity as that of the eyes of a human inspector. However, the spectral sensitivity of the linear image sensor array is limited by image sensing elements used in the sensor array. On the other hand, it is possible to easily change the spectrum of illuminating light for the cup to be inspected. In view of this, the disclosed embodiment, uses a light source emitting light having a color temperature of 2500° K. to 3200° K., such as halogen lamps and tungsten lamps, and use is made of an optical filter capable of selectively passing light components of the wavelength range in which the image sensing element has a less sensitivity than the human eye, at an increased rate compared with the passing of the remaining light components. Thus, the light after passing through the optical filter is accordingly emphasized in the above range of wavelength, compared with the natural light thereby permitting the linear sensor array to simulate the spectral sensitivity of the human eye.

When the inner surface of the paper cup is scanned in the above mentioned manner, the illumination has to be even over the whole of the inner surface portion being scanned. Therefore, it is preferable that the cup be illuminated from substantially the same direction as that of the camera 138. On the other hand, it is necessary to detect the position of the seam in the paper cup for the image information processing as mentioned hereinafter. In view of these matters, the cup is illuminated from a position apart from the optical axis of the camera to produce the shadow of the seam portion. For example, as shown in FIG. 11, the paper cup is illuminated in such a manner that when the seam 152 of the paper cup is aligned with the optical axis 146 of the camera, the seam 152 is illuminated from the side of a paper sheet portion 154 nearer to the camera. In this case, assuming that the inclined angle of the illuminating light to the optical axis 146 is "θ" and the thickness of the paper sheet 154 is "t", the width of the seam shadow is expressed by t tan θ. In order for the shadow of the seam to be surely detected by the linear image sensor array, it is preferred that the width of the image of the seam shadow formed on the linear sensor array be at least twice the width of a photosensitive area of the sensor array.

The required luminous intensity of the light source is determined on the basis of the F number of the lens, the size of the aperture, the sensitivity of the linear image sensor array, the distance between the light source and the surface to be inspected, the distance between the linear image sensor array and the surface to be inspected, etc. In order to cause the linear sensor array to surely output an image signal having a sufficient level for the image information processing, the illuminance at the cup inner surface is required to be about 250000 to 350000 luxes when the whole inner surface of one ordinary size paper cup is scanned for 0.25 seconds. In addition, if the illumination for the paper cup is not even, a so-called shading consequently appears in the image information obtained, and the detection preciseness is decreased at relatively dark portions. Particularly, since both of the side and the bottom of the paper cup do not lie in the same plane, if both the side and the bottom are illuminated by one illuminating device positioned at random, the side and the bottom would be different in illuminance. Thus, for example, the paper cup is illuminated so that the center axis of the illuminating light is in parallel to the line bisecting the angle between the bottom and the side, similarly to the case of the optical axis of the camera shown in FIG. 9A. In any case, since the paper cups to be inspected are different in size and in the ratio of height to diameter, the illuminating direction should be determined in accordance with the size and other factors of the cup to be actually inspected.

Furthermore, since the linear image sensor array has an elongated photosensitive area, a portion scanned by such a sensor array at each moment is an elongated area. Therefore, it is effective if only an elongated area of the paper cup inner surface to be inspected is evenly and concentratedly illuminated.

In view of this, for example, as shown in FIG. 12A, the illuminating device may be constructed by a point light source 156 of several Kilowatts and a cylindrical convex lens 158 capable of concentrating the light from the light source 156 to an elliptic area 160. Alternatively, as shown in FIG. 12B, the illuminating device may be constituted of the point light source 156, a spherical convex lens 162 for concentrating the light from the light source 156, a cylindrical concave mirror 164 for concentratively reflecting the light from the lens 162 to the elliptic area 160. Further, as shown in FIG. 12C, use is made of a bar light source 166 such as a halogen lamps of several Kilowatts for use in copiers and the spherical convex lens 162 for concentrating the light from the light source 166 to the elliptic area 160 located at the focal point of the lens 162.

In the shown embodiment, the method of FIG. 12B is adopted. Namely, the point light source 156 and the spherical convex lens 162 are located within the processing and discriminating apparatus 16 as shown in FIG. 1, and the light passing through the lens 162 is directed out through a hole 168 formed in the side panel of the apparatus to a cylindrical concave mirror (not shown) mounted on an inclined plate 170 of a cover secured to the side panel, so that the light reflected by the mirror illuminates the paper cup positioned in the inspection station of the conveying apparatus 10. Thus, while each paper cup is rotated about its own axis in the inspection station, the inner surface of the paper cup is scanned by the surface scanning device 14.

If it is preferred to obtain the color image of an object to be inspected and to perform the defect detection on the color image information, it is possible to obtain image signals of R, G and B or Y, I and Q in a conventional manner. This would be easily achievable to persons skilled in the art.

Figure 13:
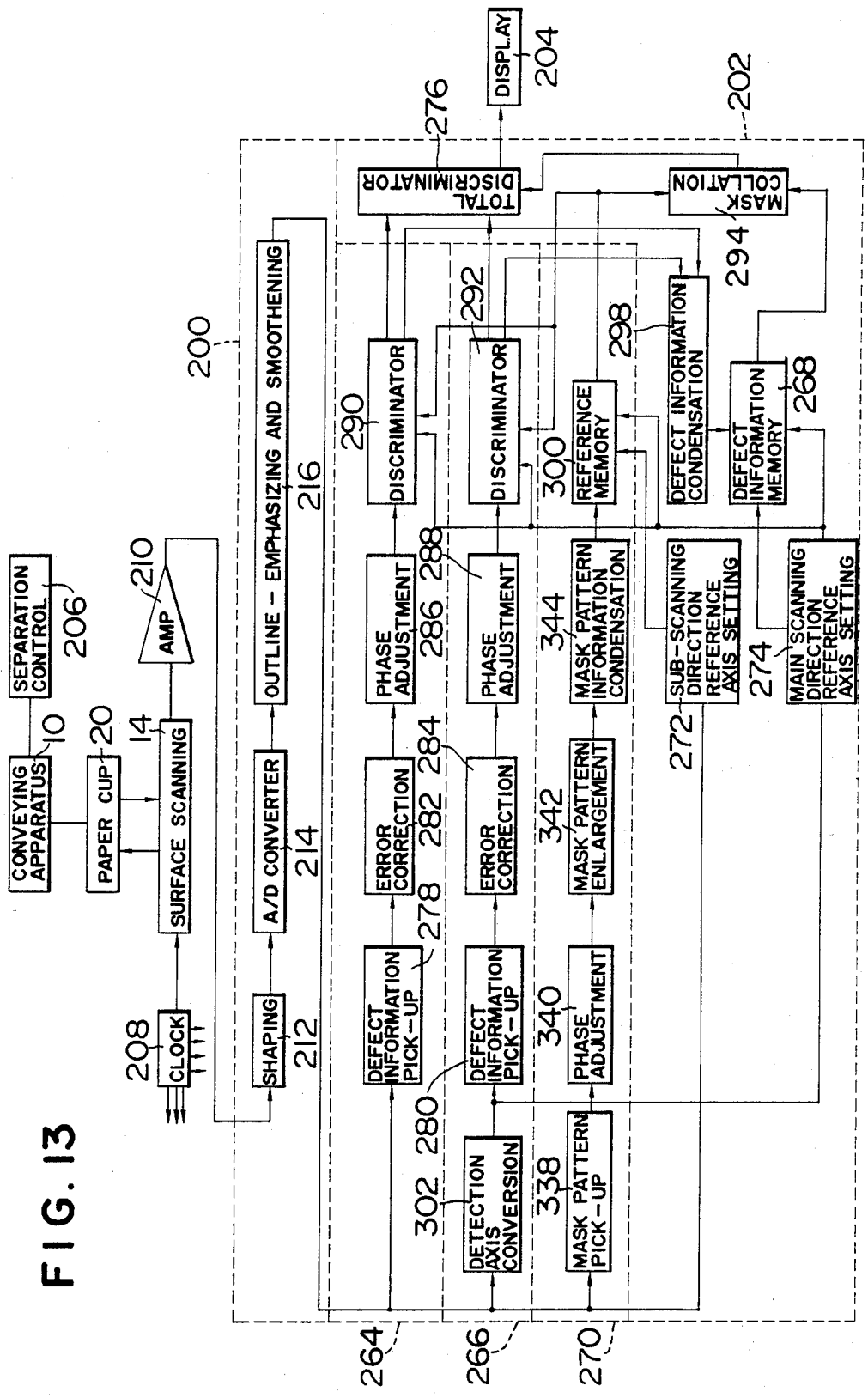
FIG. 13 is a block diagram of the detecting and processing apparatus.

The image information of the paper cup inner surface obtained in the above mentioned manner is fed to and processed by the processing and discriminating device 16 as shown in the block diagram of FIG. 13 for the purpose of discriminating whether or not any defects actually exist on the inner surface of the paper cup.

Figure 14A:
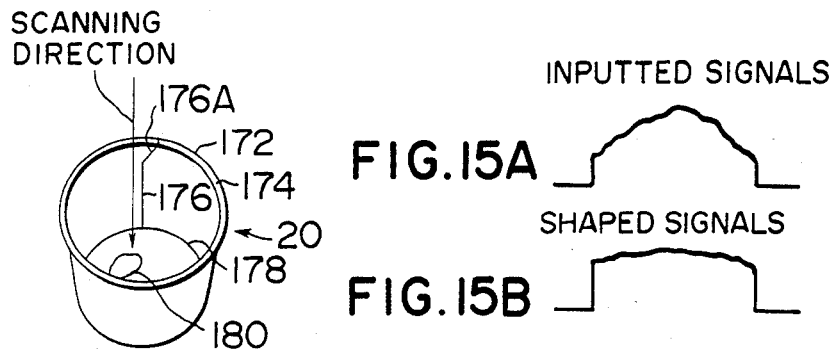
FIG. 14A is a perspective view of a paper cup.

Here, reviewing the inner the inner surface of a paper cup, the inner surface of the cup 20 has an upper edge 172, a flange 174 extending outwardly from the upper edge 172, a seam 176 in the side, a seam 178 between the side and the bottom, and a straw hole 180 formed in the bottom and covered by an easily peelable metal foil, as shown in FIG. 14A. As mentioned hereinbefore, these portions are detected when the cup is imaged, but are not defects. Therefore, in order to ensure that these non-defective portions are not regarded as being defects when the image information obtained is processed for defect detection, it is necessary to selectively deadband-treat or mask the image information portion corresponding to these non-defective portions. In this case, it is also necessary to make the size of the mask larger than the precise size of the non-defective portions by some degree, since it is impossible to completely eliminate inaccuracy in the position of the paper cup located in the inspection station, vibration of the optical system, eccentricity in the rotating paper cup, etc. However, if the image information is processed using such a large mask, there is a large degree of possibility of defects very close to the non-defective portions being masked and therefor not detected.

Figure 14B:
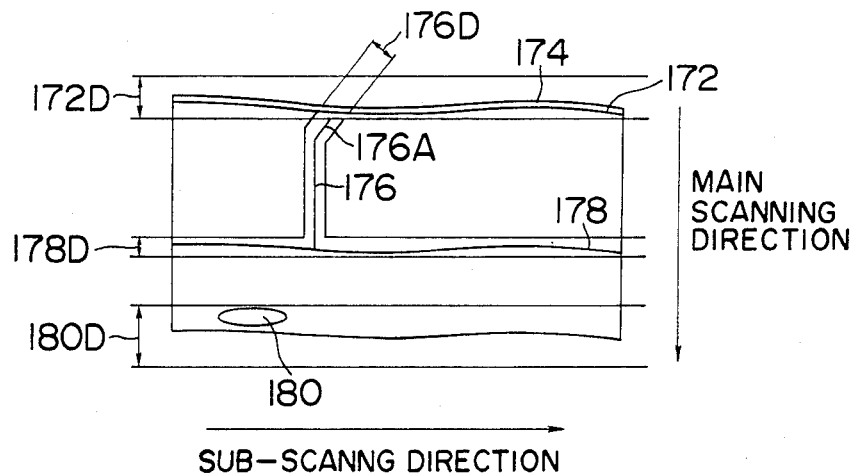
FIG. 14B is a developed view of a mask pattern for the inner surface of the paper cup as shown in FIG. 14A.

For the sake of simple consideration, one example of a simple mask pattern for the paper cup shown in FIG. 14A is shown in the developed view of FIG. 14B. FIG. 14A shows a case in which the edge 172 and the side-bottom seam 178 are slightly waved because the paper cup has been positioned to have its own center axis slightly eccentric to the rotating axis.

In the visual field, the upper edge 172 is the boundary between a dark portion and a light portion if the background is made black, and therefore, it may be detected as a defect even if it does not have any defects such as cracks or dirt. The upper flange 174 ordinarily has many small convex-concave portions on its surface formed in the flange shaping process, and the convex-concave portions may be detected as defects if the defect detection is performed in the same manner as that for detecting defects in the side surface. Therefore, it is necessay to provide a mask 172D covering the upper edge and the upper flange. Similarly, it is also necessary to provide a relatively wide mask 178D for the side-bottom seam 178. In addition, a mask is required for the bottom hole 180. But, this hole 180 appears randomly apart from the scanning start position in the developed image of the cup obtained. Therefore, it is necessary to provide a mask 180D covering all area in which the appearance of the hole 180 can be expected.

However, if such masks are used, a considerable portion of the image information will be consequently masked, so that the possibility of failing to find defects is large. Furthermore, it is also necessary to provide a mask 176D for the side seam 176 and to mask the image information portion corresponding to the side seam 176. As mentioned hereinbefore, however, there has been no effective method for performing masking for the side seam.

The processing and discriminating device 16 in the shown embodiment is capable of surely and reliably detecting any visible defects by solving the above mentioned problems.

The processing and discriminating device 16 is adapted to perform defect detection both in a main scanning direction (the scanning direction of the linear sensor array) and in a sub-scanning direction direction (the direction of the rotation about the center axis of the paper cup). In addition, it is also adapted so that a masking treatment for a non-defective portion having directivity, such as the upper edge, the upper flange, the side seam and the side-bottom seam of the paper cup, is performed in the defect detection operation of only either the main scanning direction or the sub-scanning direction, whereby no masking treatment is ever performed in the defect detection operation in the other scanning direction, so as to make the perfectly masked portion substantially zero.

Therefore, since the defect detection is performed in both the main scanning direction and the sub-scanning direction, it is possible to mask the side seam.

Furthermore, the bottom hole of the paper cup has a predetermined positional relation to the side seam. Therefore, in view of this, the device is preferably adapted to detect the side seam of each paper cup and to mask only a portion of the bottom in the predetermined positional relation to the detected side seam so that a portion not to be masked is not actually masked.

If the center axis of the paper cup is eccentric to the axis of rotation of the paper cup, the address of the image signal representative of the upper edge of the paper cup (the address number of the image sensor element counted from one end of the linear sensor array) varies from scanning to scanning. In this case, if the masking treatment is made for the upper edge on the basis of the address of the image signals, it is necessary to broaden the width of the mask. Therefore, in order to minimize the mask for the upper edge, the portion where the image signal firstly changes from the dark condition to the light condition after the start of each scanning is regarded as being the upper edge, and the starting point of the area to be inspected is determined on the basis of the upper edge, so that the inspection starting address for each scanning is changed to follow the variation in position of the upper edge from scanning to scanning. In this manner, the inspection area is set in the scanning section and the defect detection is performed only in the inspection area. If this is done, even if the center axis of the paper cup is eccentric to the axis of revolution of the paper cup, since the upper edge always takes a predetermined position in the inspection area, it is possible to minimize the mask.

The processing and discriminating device 16 which performs the above mentioned processing comprises a preprocessing-section 200 and a data processing section 202, as shown in FIG. 13. To the data processing section 202 are connected a display device 204 and a separation control device 206 associated with the conveying apparatus 10. In the case that the data pocessing section 202 outputs a defect signal, the separation control device 206 operates to cause the valve 108 to open when the paper cup that has been determined as being defective is fed to the station V of the conveying apparatus 10, so that the defective paper cup is ejected through the exhausting duct 128 by compressed air. The separation control device 206 also operates to open the valve 100 when the cup holder is positioned at the feed-out station VI, irrespectively of whether the paper cup actually is in the cup holder, so that compressed air is supplied to the bottom of the cup holder in the feed-out station IV. At that time, if a paper cup found to be good is in the cup holder, the paper cup is fed out through the feed-out duct 130.

The surface scanning device 14 comprises a linear image sensor array consisting of for example 1024 solid state image sensing elements, and outputs a picture element signal which is read out in series in synchronism with clock signals supplied from a clock circuit 208. The picture element signal is fed to a pre-amplifier 210 where it is amplified and then is outputted to the pre-processing section 200. This pre-processing section 200 includes a shaping circuit 212, an analog-to-digital converter 212 and an outline-emphasizing and smoothening circuit 216.

N analog picture element signals obtained by scanning a linear sensor array of N elements once, express a shading or so-called parabolic distortion as shown in FIG. 15A caused by convex-concave of the surface surface to be inspected, unevenness in illumination, and difference in distance between the surface to be inspected and the respective elements of the linear sensor array. This distortion is merely a gentle and gradual change in the signal level over one scanning. Therefore, the shaping circuit 212 obtains an average waveform or envelope curve, and modifies the input picture element signal as shown in FIG. 15B, on the basis of the obtained average waveform or envelope curve.

Figure 16:
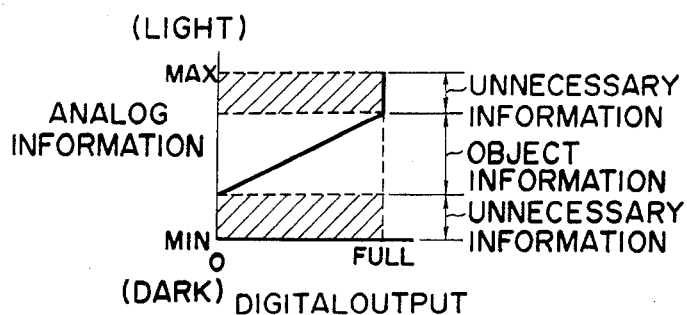
FIG. 16 is a graph showing the relation between the analog picture element signal and a digital picture element signal converted therefrom.

The A/D converter 214 converts each analog picture element signal modified as shown in FIG. 15B to eliminate the distortion, to a digital picture element signal consisting of 6 bits to 8 bits for each picture element. In this A/D conversion, it is effective if the converter disregards levels of the analog picture element signal corresponding to the background black and the pure white which do not perhaps appear in image information of the object to be inspected, and allocates all graduations that can be expressed by the digital signal to only possible analog signal levels, i.e. halftone signal levels, appearing in the image information of the object to be inspected, as shown in FIG. 16. For example, if each digital picture element signal consists of 6 bits, the lightness can be divided into 64 graduations.

The outline-emphasizing and smoothening circuit 216 selectively performs either the outline-emphasizing treatment or the smqothening treatment.

If a halftone defect D as shown in FIG. 17A is line-scanned along a line S, the obtained picture element signal varies in level as shown in FIG. 17B. Namely, the boundary between the defect D and the other portion is not clear.

The outline-emphasizing treatment is performed to sharpen the change in density at the boundary of the defect having unclear contrast as shown in FIG. 17C so as to clarify the extent of the defect, so that the information indicative of a defect can be easily and surely obtained. Therefore, by this treatment, a light small defect is emphasized to have a clear contrast, so that it can be easily detected.

In accordance with the theory of outline-emphasis, it is well-known that the Laplacean of the image f(x,y) can be expressed as follows:

$$\nabla^2 f(x,y) = \frac{\gamma^2 f(x,y)}{\gamma x^2} + \frac{\gamma f(x,y)}{\gamma y^2} \qquad (1)$$

and this Laplacean is an outline-emphasized function. In this embodiment, however, the above function is not calculated, and instead of it, the outline-emphasizing treatment for each picture element signal is performed on the basis of the difference between that picture element signal and the image information of peripheral picture elements adjacent to the picture element corresponding to that picture element signal. For example, in the outline-emphasizing treatment for a central picture element E in an image area of three lines but three picture elements for each line as shown in FIG. 18, the outline information is established by the difference between 4E and the sum of picture element information for the upper, lower, right and left picture elements B, H, F and D. Taking eight peripheral picture elements into consideration, the outline information is established by the difference between 4E and one half of the sum of picture element information for the eight picture elements A, B, C, D, F, G, H and I. This outline information is added to be image information for the picture element E so as to provide an outline-emphasized image information for the element E. In this manner, if the picture element is white, the picture element is whitened more and more, and if the picture element is black, it is blackened more and more, so that the outline of a defect is classified.

In this outline-emphasizing treatment, the image information E may be weighted by multiphying E by a coefficient K. In this case, the outline-emphasized image information for the picture element E can be obtained by adding the outline information to KE and dividing the sum by K.

The smoothening treatment is used for eliminating noises on the paper cup surface and momentary random noises generated in the photoelectric conversion system and other systems as shown in FIG. 19A to obtain a smoothened envelope of the signals for each scanning, so that error does not occur in the operation for picking up information indicative of defects. In this case, the smoothened information of the central picture element E in the image area of three lines but three picture elements in each line is expressed by the arithmetical mean of the image information for the center picture element and the four or eight peripheral picture elements. The image information for the center picture element E may be weighted by a coefficient K and the sum of KE and the information for the four picture elements or one half of the information for the eight picture elements may be divided by (K+4).

The outline-emphasizing treatment and the smoothening treatment are suitably selectively used in view of the surface condition of the product to be inspected to obtain image information which can be easily treated by the subsequent processing circuits. For example, if light defects appear or exist on a surface which does not easily generate momentary random noises, as in the case of the inner surface of a paper cup, it is sufficient to excute only the outline-emphasizing treatment. On the other hand, only the smoothening treatment is performed when there is inspected a product having a surface apt to generate momentary random noises and on which clear contrast defects may appear or exist. But, if there may appear noises of small amplitude such as paper surface noise and if defects are not clear in contrast, both the outline-emphasing treatment and the smoothening treatment may be used.

Figure 20:
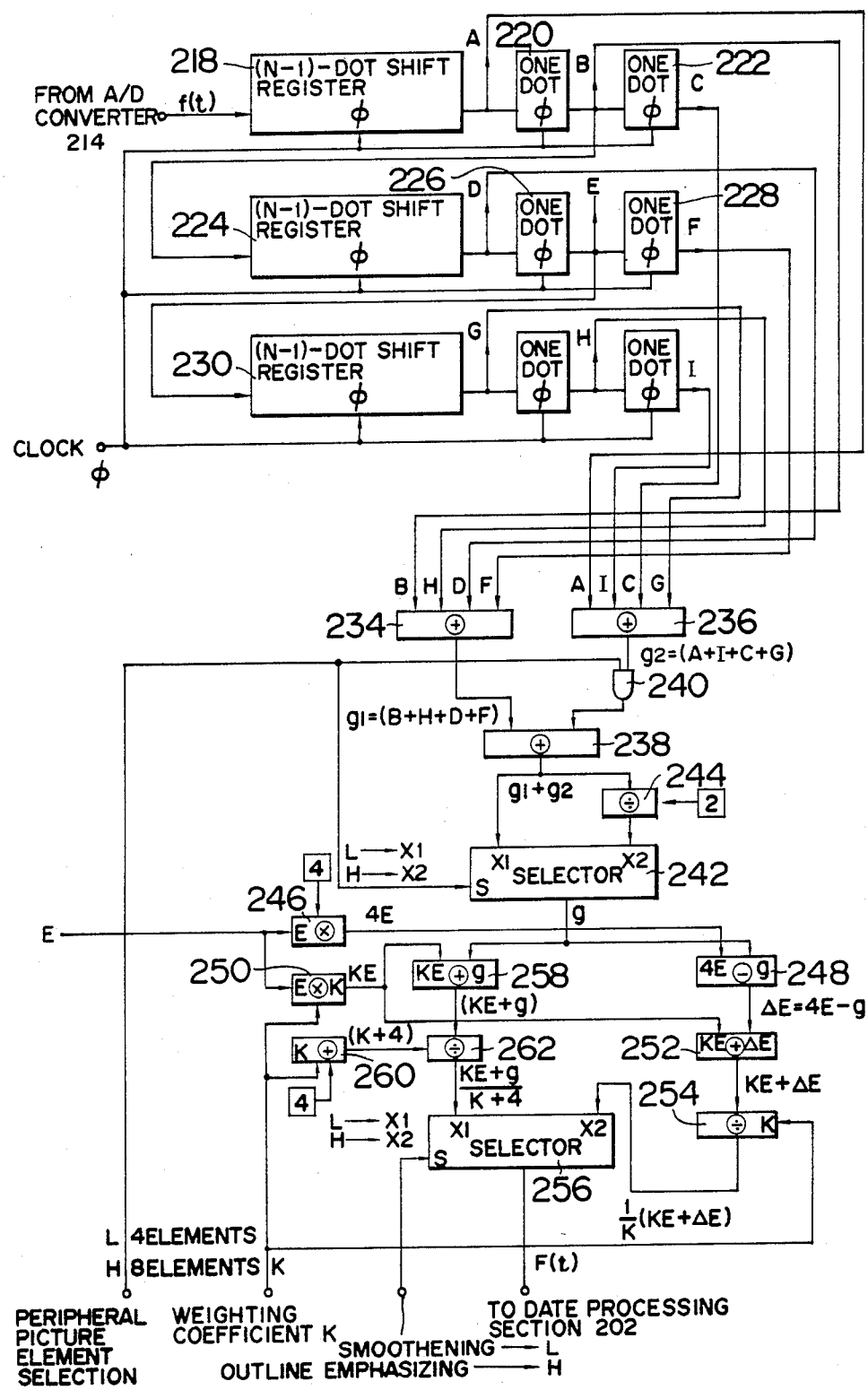
FIG. 20 is a block diagram of the outline-emphasizing and smoothening circuit.

Next, explanation will be made of the circuit construction and operation of one example of the outline-emphasizing and smoothening circuit 216 with reference to FIG. 20. Assuming that one scanning is constituted by N picture elements, the image information f(t) is fed to the input of a shift register of (N+1) dots in total consisting of a shift register 218 of (N−1) dots and two one-dot shift registers 220 and 222 which are connected in series. The output of the Nth shift register 220 is connected to an input of a second (N+1)-dot shift register including a (N−1)-dot shift register 224 and two one-dot shift registers 226 and 228. Furthermore, the output of the Nth shift register 226 is connected to an input of a third (N+1)-dot shift register composed of a (N−1)-dot shift register 230 and two one-dot shift registers. With this arrangement, the outputs of the (N−1)th, Nth and (N+1)th stages of the three (N+1)-dot shift registers respectively provide image information for the picture elements A, B, C, D, E, F, G, H and I having the positional relation as shown in FIG. 18. Therefore, image information for nine picture elements in three adjacent scanning lines and adjacent to one another in the sub-scanning direction can be obtained from the newest portion of the image information f(t) continuously supplied from the A/D converter 214. Since the image information is sequentially fed to the shift register array, the information for the respective picture elements is successively outputted as the picture element information A, B, C, D, E, F, G, H and I in the mentioned order. The image information for three lines but three picture element in each line is selectively supplied to adding circuits 234 and 236.

The adding circuit 234 receives the image information for the upper, lower, left and right picture elements B, H, D and F and outputs the sum $g_1$ as expressed as follows:

$$g_1 = B + H + D + F \qquad (2)$$

The adding circuit 236 receives the image information for the four obliquely adjacent picture element A, I, C and G and seeks the sum $g_2$ as expressed as follows:

$$g_2 = A + I + C + G \qquad (3)$$

For considering the eight peripheral picture elements, the output of the adding circuit 234 is connected to one input of two-input adder 238, and the output of the adding circuit 236 is connected to the other input of the adder 238 through an AND gate 240. The output of the adder 238 is connected to one input XI of a selection circuit 242 and a divider 244 whose output is connected to the other input X2 of the selection circuit 242. If only the four peripheral picture elements are considered, a low-level selection signal is fed to the AND gate 240 so as to close the gate and also supplied to the selection circuit so as to cause it to select and output the information inputted to the input XI. Therefore, in this case, the adder 238 outputs the information $g_1$ and the selection circuit 242 also outputs the information $g_1$ as the peripheral picture element information g.

$$g = g_1 = (B + H + D + F) \quad (4)$$

On the other hand, if the eight peripheral picture elements are considered, a high-level selection signal is supplied to the AND gate 240 to open the gate and also to the selection circuit 242 so as to cause it to select and output the information inputted to the input X2. Therefore, the adder 238 receives the information $g_1$ and $g_2$ to output $(g_1 + g_2)$ to the divider 244, where the information $(g_1 + g_2)$ is divided by the constant "2", and then fed to the input X2 of the selection circuit 242. The selection circuit 242 outputs the information $(g_1 + g_2)/2$ as the peripheral picture element information g.

$$\begin{aligned} g &= (g_1 + g_2)/2 \\ &= (A + B + C + D + F + G + H + I)/2 \end{aligned} \quad (5)$$

The image information for the picture element E is supplied to a multiplying circuit 246 where it is multiplied by the constant "4" so as to output the information 4E to one input of a subtracter 248 whose another input is connected to the output of the selection circuit 242. Therefore, the subtracter 248 outputs the outline information $\Delta E$:

$$\Delta E = 4E - g \quad (6)$$

The image information for the picture element E is also fed to another multiplying circuit 250 where it is multiplied by a weighting coefficient K so as to supply the weighted information KE to one input of an adder 252 whose other input is connected to the output of the subtracter 248. Therefore, the adder 252 outputs the information $(KE + \Delta E)$ to a divider 254 where it is divided by the weighting coefficient K so as to produce the outline emphasis picture element information F(t):

$$\begin{aligned} F(t) &= \frac{1}{K}(KE + \Delta E) \\ &= \frac{(K+4)E - g}{K} \end{aligned} \quad (7)$$

This outline-emphasis picture element information F(t) is fed to one input X2 of another selection circuit 256 and outputted from the same selection circuit 256 when a high-level selection signal is supplied to the selection circuit 256.

The information KE supplied from the multiphying circuit 250 is also fed to one input of an adder 258 whose other input is connected to the output of the selection circuit 242. Therefore, the adder 258 outputs the information $(KE + g)$ to a divider 262. The weighting coefficient K is also fed to one input of an adder 260 which receives the constant "4" at the other input thereof to supply the information $(K + 4)$ to the divider 262. Therefore, the divider 262 outputs the smoothened picture element information F(t):

$$F(t) = \frac{KE + g}{K + 4} \quad (8)$$

This smoothened picture element information F(t) is fed to the other input X1 of the selection circuit 256 and is outputted from the same selection circuit 256 when a low-level selection signal is supplied to the selection circuit 256.

Whether the four or the eight picture elements should be picked up as the peripheral elements, whether the smoothening or the outline-emphasizing should be made, and the valve of the weighting coefficient K, may be manually or automatically selected in accordance with the surface condition of a product to be surface-inspected.

The digital picture element signal of 6 bits to 8 bits for each picture element pre-processed as mentioned above is supplied to the data processing section 202.

This data processing section comprises a pair of defect information detecting circuits 264 and 266 for detecting defects on the product being inspected, a memory 268 for storing the defect information, a mask pattern circuit 270 for producing mask patterns for non-defective portions such as seams, marks and characters on the surface to be inspected, a pair of reference axis setting circuits 272 and 274 for determining a reference axis which can be used for determining the portion to be masked or for partitioning the extent of the area in which the defect detection is performed, a total discriminating circuit 276 for determining whether the inspected product is defective or non-defective on the basis of the obtained and processed information, and a mask collation circuit 294 for collating the obtained defect information with the mask pattern. The defect information detecting circuits and the reference axis setting circuits are respectively provided for the main scanning direction and for the sub-scanning direction.

In the pre-processing section, the picture element signal is modified to compensate for waveform or envelope distortion by the shaping circuit 212 and is smoothened to suppress the amplitude of noises by the outline-emphasizing and smoothening circuit 216 when the smoothening is selected. But, the noise cannot be completely removed, so that the waveform or envelope distortion and the noise will inevitably remain to some extent in the signal fed to the date processing section 202. Thus, the defect information detecting circuits 264 and 266 respectively include defect information pick-up circuits 278 and 280 adapted to effectively remove the remaining envelope distortion and the remaining noise so as to enable sure detection of a light defect buried in the noise. In addition, there are provided error information correction circuits 282 and 284 adapted to remove still remaining isolated noises and image information on very small allowable defects. Phase correction circuits 286 and 288 are provided to delay the defect information so as to coordinate it in phase with the information most delayed in phase in the data processing section 202. Discriminating circuits 290 and 292 further remove image information on relatively large but allowable defects and collate the finally obtained defect information with the mask pattern so as to output only the defect information required for determining whether the inspected product is defective or non-defective.

The defect information pick-up circuits 278 and 280 are constructed to obtain a dynamic average of the inputted digital picture element information, to remove the waveform or envelope distortion and the noise from the inputted information by using the obtained dynamic average, and to detect not only clear defects but also defects not having a sufficient contrast by using suitably predetermined threshold levels. The term "dynamic average" is used in the specification and the claims to mean that the dynamic average of the concentration on one picture element is an average of the respective concentrations on the one picture element and on picture elements in one-dimensional or two-dimensional area surrounding the one picture element. Now, considering the one-dimentional dynamic average in the inputted picture element information $a_K$ as shown in FIG. 21A, the dynamic average $A_K$ for the information $a_K$ is expressed by the average of the picture element information on the picture elements in the interval of $-n$ to $+n$ centering around the picture element corresponding to the information $a_K$.

$$A_K = \frac{1}{2n} \sum_{i=-n+1}^{n} a_{K+i} \qquad (9)$$

This dynamic average $A_K$ is also shown in FIG. 21A. Since the dynamic average can be regarded as showing the envelope distortion in the interval of the dynamic average, the difference $d_K$ between the inputted information $a_K$ and the dynamic average $A_K$ can be also regarded as a picture element signal from which the envelope distortion has been removed.

$$d_K = a_K - A_K \qquad (10)$$

The difference $d_K$ is shown in FIG. 21B. If the information $d_K$ thus obtained is compared with a sufficiently low threshold value $TH_1$ sufficiently smaller than an average level of the information $d_K$ as shown in FIG. 22A so as to obtain a pulse $S_1$ as shown in FIG. 22B, the pulse $S_1$ corresponds to a dark defect.

On the other hand, even if a light defect D having a relatively large extent as shown in FIG. 23A is compared with the threshold value $TH_1$, it cannot be detected because it is sufficiently lighter than the lightness indicated by the threshold value $TH_1$. But, all the picture element signals corresponding to the defect D have levels biased in the same direction as seen from FIG. 23A. Thus, the dynamic average $D_K$ for the information $d_K$ is obtained as shown in FIG. 23B.

$$D_K = \frac{1}{2d} \sum_{i=-d+1}^{d} d_{K+i} \qquad (11)$$

Then, the dynamic average $D_K$ is compared with a second threshold value $TH_2$ which is greater than the first threshold value $TH_2$ but is slightly smaller than the average level of the dynamic average information $D_K$ to obtain a pulse $A'$ as shown in FIG. 23C. Since width of this pulse $A'$ is considered to be smaller than the actual extent of the defect D, the pulse $A'$ is enlarged in width to obtain a pulse A as shown in FIG. 23D. Only in the interval determined by the width of the pulse A, the information $d_K$ is compared with a third threshold value $TH_3$ slightly smaller than the average level of the information $d_K$ as shown in FIG. 23E, so as to obtain a pulse $S_2$ showing the light defect D as shown in FIG. 23F. In this case, since a noise N appears out of the interval determined by the pulse A, only the light defect D is detected.

The threshold values $TH_1$, $TH_2$ and $TH_3$ used in the aforementioned processing should be determined on the basis of what concentration of defect should be detected. Therefore, the system is preferably designed so that these threshold values can be set on the basis of the nature of the surface of the product to be inspected and the acceptable degree of defect.

Each of the defect information pick-up circuits 278 and 280 performs the above mentioned data processing to pick up only the defect information. In addition, each of these circuits outputs the image information including the defect information in the form of a binary signal for each picture element, so as to make the subsequent data processing easier. For example, the balck is expressed by the logical level "1" and the white is expressed by "0".

Figure 24:
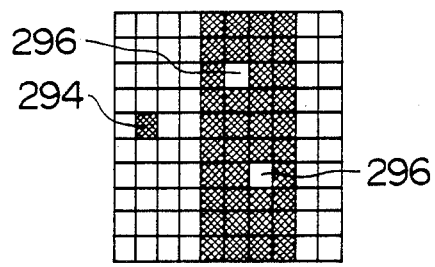
FIG. 24 diagrammatically shows so-called "hole" and "patch" in the image information.

In the binary image information supplied from each of the defect information pick-up circuits 278 and 280, the noise has been already considerably removed, but there still exist an isolated noise 294 and isolated "holes" 296 corresponding in size to one picture element as shown in FIG. 24 and also "holes" and "patches" which are larger than the isolated noise 294 and the isolated holes 296 but cannot be regarded as a defect.

The error information correction circuits 282 and 284 are provided to eliminate the above mentioned noises and "holes". Firstly, the isolated noise or "hole" can be removed by logical processing. For example, assuming that the image information on the picture element on the coordinate (I,J) is expressed by F(I,J), the following G(I,J) is sought:

$$G(I,J) = \overline{F(I-1,J)} \cdot \overline{F(I+1,J)} \cdot \overline{F(I,J-1)} \cdot \overline{F(I,J+1)} \qquad (12)$$

where $\overline{F(I,J)}$ is a complement of $F(I,J)$.

In this case, if the black and the white are expressed by the logical levels "1" and "0", respectively, when $G(I,J)=1$ and $F(I,J)=1$, the point (I,J) is an isolated noise, and therefore, the binary image information for the point (I,J) is corrected to the logical level "0". By this method, an isolated "hole" is also removed or corrected.

Figure 25A:
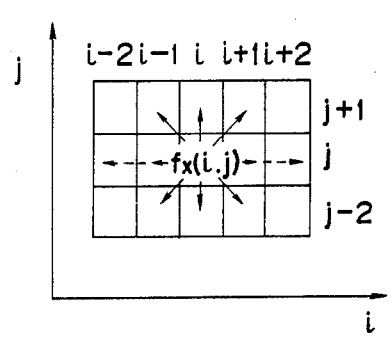
FIGS. 25A and 25B diagrammatically illustrate the extent of the picture elements sampled in a "mesh-filter" processing.
Figure 25B:
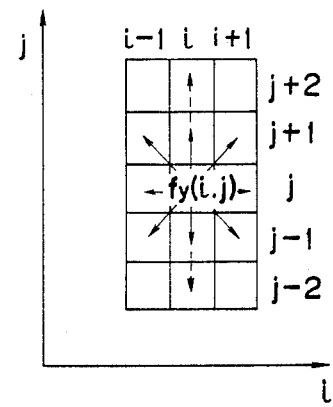

"Patches" and "holes" larger than the isolated noise are discriminated and removed by a so-called "mesh filter". The mesh filter is adapted to check the continuity in the image information between one picture element f(i,j) and an adjacent picture element to the one picture element to learn the size of the "patch" or the "hole" and to remove it if it is smaller than a predetermined size. FIGS. 25A and 25B show the extent of a two-dimensional image area inspected with respect to the continuity by a main scanning direction mesh filter and a sub-scanning direction mesh filter, respectively, which are used in the error information correction circuits 282 and 284, respectively.

As seen from FIGS. 25A and 25B, the main scanning direction mesh filter inspects the continuity over an extent longer in the main scanning direction than in the sub-scanning direction, and the sub-scanning direction mesh filter inspects the continuity over an extent elongated in the sub-scanning direction. The size of a "patch" or "hole" that should be regarded as being non-defective by the mesh filter would depend upon the nature of the product to be inspected and the acceptable degree of defect. Therefore, it is preferred to be able to adjust the extent inspected by the mesh filter, step by step.

The phase adjusting circuits 286 and 288 operate to coordinate the binary picture element signals outputted from the error information correction circuits 282 and 284, in phase with the most phase-delayed signal among the signals supplied from the circuits 270, 272, 274, 282 and 284, namely, the signal from the sub-scanning direction reference axis setting circuit 272, so that all signals are in phase in the subsequent data processing.

The discriminating circuits 290 and 292 detect a defect not less than a predetermined size that is set larger than the maximum size of the "patch" or "hole" removed in the error information correction circuits 282 and 284, and at the same time erase defect information of a size less than the predetermined size. Namely, these discriminating circuits output only the defect information showing a defect or defects not less than the predetermined size. For this purpose, each of the discriminating circuits is adapted to investigate continuity in an image area constituted of for example fifteen picture elements with five elements in the main scanning direction and three elements in the sub-scanning direction. For example, when all of the fifteen picture elements indicate a defective condition, it is regarded as a defect. In any case, the extent of the picture elements sampled for discriminating a defect, and the reference number of picture elements indicating the defective condition sufficient for determining that a defect exists, would depend upon the nature of the product to be inspected and the required accuracy.

These discriminating circuits 290 and 292 output the respective defect information to a defect information condensing circuit 298 until a mask pattern information is supplied from a reference memory 300 which will be explained in detail hereinafter. Therefore, the defect information is condensed by the information condensing circuit 298 and then fed to the defect information memory 268 where it is stored. This information condensation is effective in reducing the required capacity of the memory 268. When the sub-scanning direction reference axis setting circuit 272 detects a reference axis in the sub-scanning direction and outputs a reference axis detection signal to the reference memory 300, the memory 300 starts to supply the mask pattern information to the discriminating circuits 290 and 292. Each of the discriminating circuits 290 and 292 collates the finally obtained defect information with the mask pattern information from the reference memory 300 to output only the defect information that has not been masked by the mask pattern, to the total discriminating circuit 276. The total discriminating circuit 276 determines, on the basis of the defect information from the discriminating circuits 290 and 292 and the mask collating circuit 294, whether or not a defect exists or whether or not the amount of defects is greater than a reference amount, and then supplies a defective signal or a non-defective signal to the separation control device 206.

The defect information detection circuits 264 and 266 operate in the same manner as mentioned above, except that the sub-scanning direction defect information detecting circuit 266 has a detection axis conversion circuit 302 as a first stage.

This conversion circuit 302 comprises n shift registers 304 of N dots connected in series as shown in FIG. 26, since one scanning in the main scanning direction is constituted by the N picture elements. The output of each of the n shift registers 304 is also connected to an adder 304A having an output thereof connected to a divider 304B. Thus, the divider 304B divides the output value from the adder 304A by n. With this arrangement, an average of all the outputs of the n shift registers 304 is outputted as a dynamic average of the image information of the picture element outputted from the center shift register of the n shift registers 304. Since each shift register 304 holds the image information of the picture elements of the number corresponding to the one scanning in the main scanning direction, the outputs of the n shift registers 304 correspond to n picture elements aligned in the sub-scanning direction. Therefore, since the n shift registers are connected in series, the dynamic-averaged picture element signal, that is expressed by the average of the signal of the n picture elements in the sub-scanning direction, is sequentially supplied in the order of the main scanning direction to the defect information pick-up circuit 280. In this dynamic average in the sub-scanning direction, the image information of a detectable linear element extending in the main scanning direction is suppressed or erased, but the image information of a detectable linear element extending in the sub-scanning direction is maintained. Therefore, it can be theoritically said that, a detectable element extending in the sub-scanning direction, including a defect and a non-defective portion, can be detected by investigating the picture element signal dynamic-averaged in the sub-scanning direction. As seen from the above, this detection axis conversion circuit 302 is adapted to supply the picture element signal dynamic-averaged in the sub-scanning direction in the order of the main scanning direction, instead of actually performing orthogonal transformation of the coordinate.

Each of the reference axis setting circuits 272 and 274 operates to provide a reference line which can be used as a reference when the surface to be inspected is divided into several sections, when a portion to be masked is separated from the other portion and is collated with a mask pattern, and when a portion to be masked should be positionally specified in the obtained image information. The necessity for this reference axis depends upon the configuration of the product to be inspected, the position and the number of mask patterns and the scanning method. But, if no mask treatment is necessary or if a portion to be masked appears at a predetermined position in the obtained image information without exception, it is not necessary to find a reference axis. In the disclosed embodiment, the main scanning direction and the sub-scanning direction reference axis information obtained is supplied to the discriminating circuit of the defect information detections circuit, the defect information memory and the reference memory.

In finding a reference axis, there can be used a linear element which can be surely detected from the image information of the product to be inspected, such as the edge of the product, a fold line, a cut line, a concave or convex line, a seam or a printed line which extends in parallel to the main scanning directions or the sub-scanning direction. In this case, if the linear element has a sufficient contrast and a sufficient thickness or width to enable its detection even if it is bent to a small extent or is slightly inclined to the main scanning direction or the sub-scanning direction, the linear element can be easily detected by using a simple comparator. But, if the image information includes many background noises and distortion, it is preferred to obtain the dynamic average as explained in connection with the defect information pick-up circuit and to detect the linear element on the basis of the difference between the inputted image information and the obtained dynamic average. In any case, it can be said theoritically said that a reference axis in parallel to the main scanning direction, i.e., a reference point in the sub-scanning direction, can be detected from the pre-processed image information, and a reference axis in parallel to the sub-scanning direction, i.e., a reference point in the main scanning direction can be detected from the output of the detection axis conversion circuit 302. If a thin linear element not having a sufficient contrast, such as a seam of a paper cup, can be used as a reference axis, it can be detected by using so-called signal accumulation technique.

In the disclosed paper cup surface inspection system, the upper edge of the paper cup is used as the reference point in the main scanning direction. For this purpose, the main scanning direction reference axis setting circuit 274 is adapted to detect, as the upper edge of the paper cup, the portion where the picture element signal firstly changes from the condition indicative of the dark to the condition indicative of the light after the start of each scanning in the main scanning direction. The circuit 274 then supplies the detection signal to the discriminating circuits 290 and 292, the reference memory 300 and the defect information memory 268.

Referring to FIG. 27, there is shown a block diagram of a seam detecting circuit which can be used in the sub-scanning direction reference axis setting circuit 272. Also referring to FIG. 28A, there is shown a developed view of the inner side surface of the paper cup shown in FIG. 14A. If the seam S is line-scanned, the level of all the picture element signals "r" obtained from the one scanning is low overall, as compared with the level of picture element signals obtained when other portions are scanned, as seen from FIG. 28B. On the other hand, when one scanning is performed to pass through the defect D, the level of the picture element signals obtained from the one scanning at that time is low only in a portion corresponding to the defect D. Therefore, the seam detecting circuit includes an accumulating circuit 306 for totalizing all the digital picture element signals for each scanning to output a total signal having the value as graphically shown in FIG. 28C. As seen from FIG. 28C, the total of the picture element signals of one scanning obtained when the seam is line-scanned is distinguishably smaller than that of picture element signals of one scanning for other portions even if the portion has a black defect. Therefore, the seam is detectable in accordance with this manner.

The total signal for each scanning thus obtained is supplied to an emphasizing circuit 308 which is adapted to compare the total signal with a threshold value TH4 as shown in FIG. 28C so as to output a difference signal fv. By the difference signal fv, the contrast between the seam and the other portions is emphasized.

The difference signal fv is fed to a reference line detecting circuit 310 where the dynamic average Av of each difference signal is calculated and then compared with the difference signal fv to output a second difference signal $r_v$:

$$r_v = fv - Av \quad (13)$$

If the difference $r_v$ becomes negative and its absolute value equals to or is greater than a predetermined reference value, the scanning line corresponding to the first difference signal fv providing the difference $r_v$ is determined as the reference axis. An output circuit 312 connected to the detecting circuit 310 provides a signal indicative of the reference axis in the sub-scanning direction.

Figure 29:
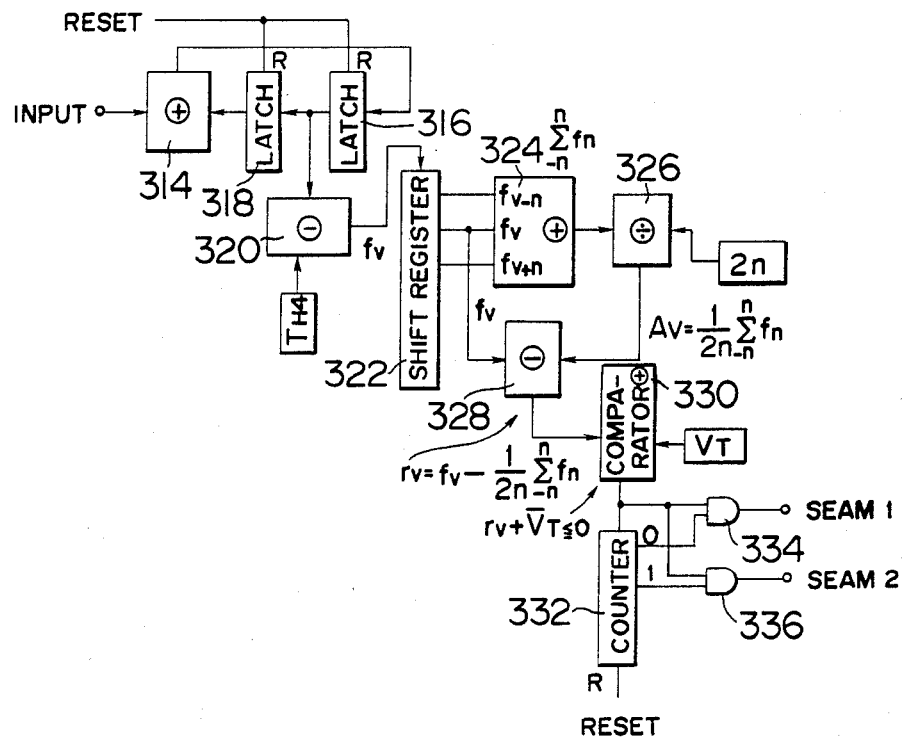
FIG. 29 is a block diagram of a reference axis detecting circuit.

FIG. 29 is a circuit diagram showing a specific example of the sub-scanning direction reference axis setting circuit 272 adapted to detect the side seam of the paper cup. The digital picture element signal from the outline-emphasizing and smoothening circuit 206 is fed to one input of an adder 314 whose output is connected to a latch circuit 316. This latch circuit 316 has an output connected to another latch circuit 318 whose output is connected to the other input of the adder 314. Therefore, the inputted digital picture element signal is added or accumulated by the adder 314 by the help of the latch circuits 316 and 318 at every application of the picture element signal. But, the latch circuits 316 and 318 are reset at the termination of each scanning, so that the latch circuit 316 supplies a total value of the picture element signals for each scanning, to a subtractor 320. The total value is subtracted by a predetermined constant value TH4 in the subtractor 320 to generate contrast-emphasized digital information fv. This information fv is fed to a 2n-dot shift register 322. The output of each stage of this shift register is connected to an adder 324 so that the adder 324 outputs the total value of the outputs of all the respective stages of the shift register 322, to a divider 326. This divider divides the inputted total value by 2n to output the a dynamic average Av over the 2n scanning lines to one input of a subtractor 328 whose other input is connected to the nth stage of the shift register 322. Therefore, the subtractor 328 calculates the equation (13) as mentioned above to supply the difference $r_v$ to one input of another adder 330, whose other input is adapted to receive a threshold value Vt. If the total value fv corresponds to the scanning line passing on the side seam of the paper cup, the difference $r_v$ is negative. Therefore, the adder 330 outputs the seam detection signal when $r_v + VT \leq 0$.

The inner surface of the paper cup is inspected while rotating the paper cup about its own axis by more than one revolution. Therefore, the side seam is detected one or twice for each paper cup. In order to distinguish the first and second detections of the same side seam, the output of the adder 330 is connected to a counter 332 and a pair of AND gates 334 and 336, which are in turn connected at the other input thereof to the "0" output terminal and the "1" output terminal of the counter 332. With this arrangement, the first seam detection signal from the adder 330 causes the counter 332 to output a high level logical signal from its "0" output terminal so as to open the AND gate 334. Thus, the AND gate 334 supplies the first seam detection signal. When the adder 330 outputs the second seam detection signal to the counter 332, the counter supplies the low level logical signal from its "0" output terminal and the high level logical signal from its "1" output terminal. As a result, the AND gate 334 is closed and the AND gate 336 is opened to output the second seam detection signal. The counter 332 is then reset at completion of the inspection of each paper cup.

The mask pattern circuit 270 comprises, as shown in FIG. 13, a mask pattern pick-up circuit 338, a phase adjusting circuit 340, a mask pattern enlarging circuit 342, a mask pattern information condensing circuit 344 and the reference memory 300 for storing the condensed mask pattern information. Ordinarily, prior to the actual inspection, a mask pattern for a product to be inspected is prepared, for example, by black-painting or cutting away the portion to be masked of a non-defective product to cause it to have a sufficient contrast and then scanning the product thus formed by the same scanning device as that used when the surface inspection is executed. Since the image information so obtained has a sufficient difference in level between the black portion and the white portion, the mask pattern pick-up circuit 338 can be constructed by a simple threshold circuit or comparator which is for example adapted to compare a reference value with the digital picture element signal from the outline-emphasizing and smoothing circuit 216 and to output a binary signal indicative of the picture element of not less than the reference value. The binary mask pattern signal is fed to the phase adjusting circuit 340 where it is brought into phase with the signal from the sub-scanning direction reference axis setting circuit 272, as mentioned in connection with the phase adjusting circuits of the defect information detecting circuits 264 and 266.

As mentioned hereinbefore, since the obtained image information includes information on the portion to be masked, it is necessary to surely and accurately remove or erase the information on the portion to be masked. But, because of irregularity in the products to be inspected and eccentricity of the center axis of the product to the revolution axis, it is very difficult to make the mask pattern completely coincident with the portion to be masked in the obtained image information. If complete coincidence cannot be obtained, the information on the portion to be masked will be regarded as being defect information. In order to avoid such misjudgment, it is preferred that the mask pattern be enlarged to some extent beforehand, so that the portion to be masked is actually surely masked irrespectively of the irregularity and eccentricity mentioned above. For this purpose, the mask pattern enlarging circuit 342 is provided.

When the mask pattern is large or extends over the full surface to be inspected, if the mask pattern information is condensed, the required capacity of the reference memory can be made small. Therefore, the mask pattern information condensing circuit 344 is provided.

In many cases, a portion to be masked lies in a limited portion on the product surface. In such a case, it is preferable that it is sufficient if the memory 300 has only a storage capacity corresponding to the limited portion. In addition, if the mask pattern is separated into a few patterns, a reference memory may be provided for each mask pattern.

As will be explained hereinafter, after the reference axis in the sub-scanning direction is detected, the discriminating circuits 290 and 292 perform real-time collation of the detected defect information with the mask pattern information so as to remove or erase the defect information corresponding to the portions to be masked and to output the remaining defect information to the total discriminating circuit 276, and then, after the surface scanning is completed, the mask collating circuit 294 operates to collate the mask pattern information and the defect information stored in the memory 268 from the start of the surface scanning to the detection of the reference axis, so as to remove or erase the defect information corresponding to the portions to be masked and to output the remaining defect information to the total discriminating circuit 276.

Figure 30:
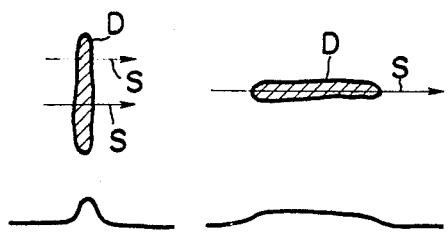
FIG. 30 illustrates the relation between the dynamic average value and the direction of the defect area in relation to the scanning direction.

Next, explanation will be made of relation between the directivity of the defect and difficulty of the defect detection, and masking treatment for the seam in the main scanning direction and the seam in the sub-scanning direction together with the method of detecting a defect in the proximity of the seam. If an elongated defect D extends in a direction perpendicular to the main scanning direction S as shown in FIG. 30, the difference signal between the inputted image information and the dynamic average thereof shows a clear difference in level between the portion corresponding to the defect $D_1$ and the other portion. Therefore, such a defect can be easily detected. On the other hand, if an elongated defect $D_2$ extends along the main scanning direction S, the difference signal between the inputted image information and the dynamic average thereof does not show a clear difference in level between the defect $D_2$ and the other portions. Therefore, such a defect cannot be detected unless the so-called "accumulation manner" is used.

It will be noted from the above that the upper edge 172 and the side-bottom seam 178 of the paper cup is detected as a defect by the scanning of the main scanning direction. Therefore, it is necessary to mask the side-bottom seam in the main scanning direction defect information detecting operation. On the other hand, since the side seam 176 is detected as a defect by the scanning in the sub-scanning direction, it is necessary to mask the side seam in the sub-scanning direction defect information detecting operation.

Ordinarily the seam of a paper cup is thin and has only a relatively small contrast. Therefore, if the scanning is performed in the longitudinal direction of the seam, it is more difficult to detect the seam than to detect the light defect as mentioned above. In addition, since the paper cup is sufficiently illuminated to be able to detect the upper edge 172 of the paper cup by the change point from the dark to the light in the main scanning direction scanning, the edge itself has only a very small contrast along the edge. Therefore, if the scanning is executed along the upper edge, it is difficult to detect the upper edge as in the case of the seam. Accordingly, the threshold values as explained in connection with the defect information pick-up circuits are adjusted so that even light defects can be detected but neither the upper edge nor the seam can be detected. With this adjustment, the upper edge 172 and the side-bottom edge 178 will not be detected by the sub-scanning direction defect information detecting operation, and the side seam 176 will also not be detected by the main scanning direction defect information detecting operation. Thus, it is unnecessary either to mask the upper edge 172 and the side-bottom seam 178 in the defect information processing for the sub-scanning direction, or to mask the side seam 176 in the defect information processing for the main scanning direction. Therefore, a defect in the proximity of the upper edge or the side-bottom seam can be effectively detected by the sub-scanning direction defect information detecting operation, and a defect near to the side seam can be also detected by the main scanning direction defect information detecting operation. But, it is necessary to mask an inclined portion 176A of the side seam in both the main scanning direction and the sub-scanning direction, since it is inclined to both the scanning directions.

Figure 31:
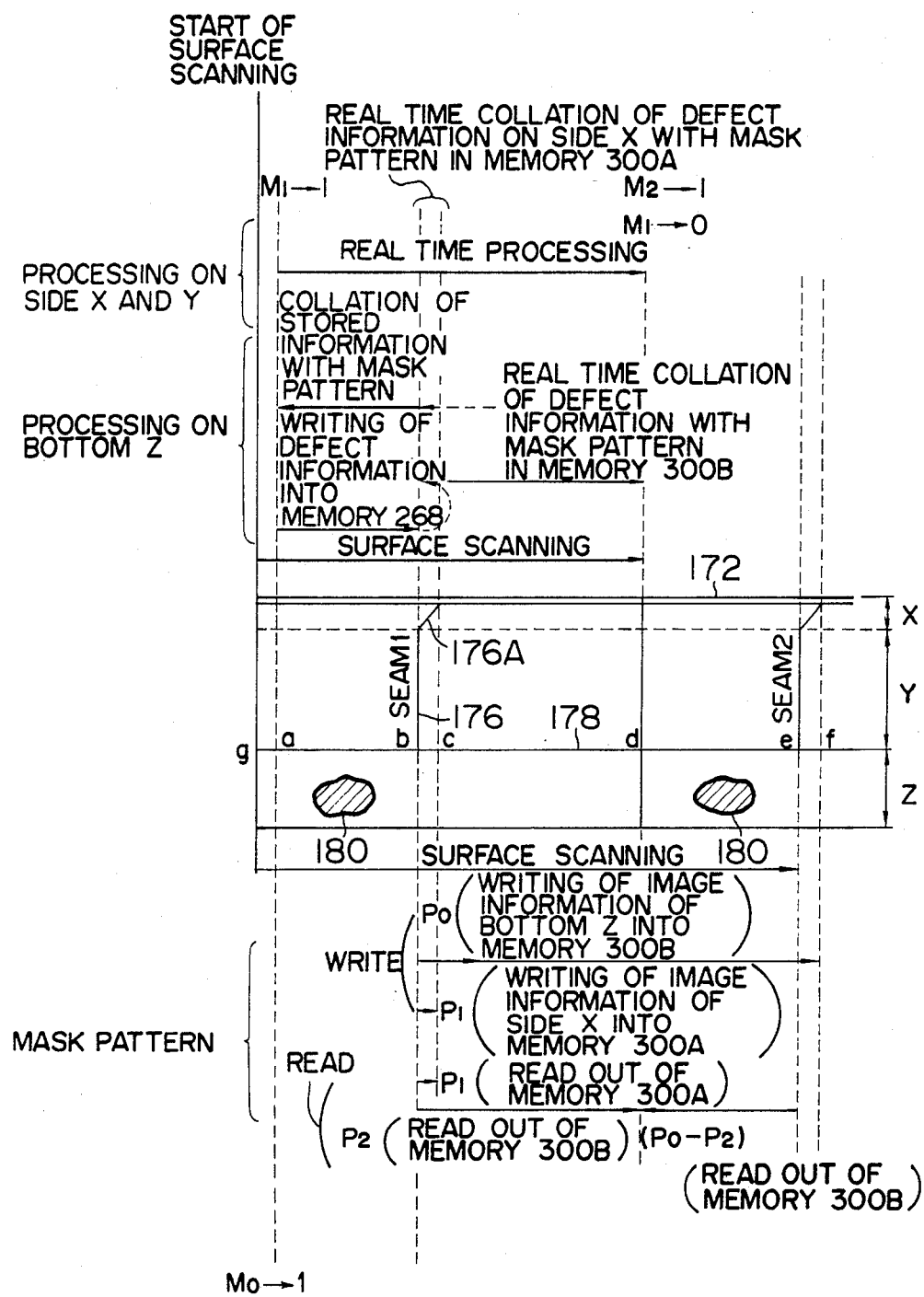
FIG. 31 is a developed view showing the relation between the scanning for the paper cup, the mask pattern storing operation and the defect detecting operation.

Referring to FIG. 31 there is shown a developed view illustrating an image obtained when the paper cup as shown in FIG. 14A is line-scanned in the method as shown in FIGS. 9A and 9B while rotating the paper cup about its own axis more than one revolution. Also, referring to FIG. 32, there is shown a circuit diagram of a principal portion of the mask pattern circuit 270. When a mask pattern information is prepared and stored, the defect information detecting circuits 264 and 266 are not used. Firstly, a paper cup provided with a mask pattern having a sufficient and clear contrast by the aforementioned manner is put and fitted into the cup holder 22 at the inspection station IV and is caused to rotate about its own axis. Then, a high-level logical signal is supplied to a mask pattern preparation command input Mo of the mask pattern circuit 270, and a pair of mode selectors 350 and 352 are set to supply the since a side portion Y covering the vertical side seam 176 has no portion to be masked, it is possible to process the image information corresponding to this portion in real time. It is necessary to perform the masking treatment in the image information corresponding to a side portion X covering the inclined seam 176A. But, as will be stated in detail hereinafter, since the final defect information detecting operation is performed after the detection of the vertical side seam 176, the defect information detecting operation for this portion to be masked is always executed after the detection of the side seam 176, i.e., the main-scanning direction reference axis. If the processing is performed in such a manner, it is possible to process the information for the portion X in real time, and, also, it is sufficient if the memory 300A has a storage capacity enough to cover only the inclined seam 176A.

The hole 180 in the bottom portion Z is always in a position in a predetermined relation to the side seam 176. Therefore, it is possible to process the image information corresponding to the bottom portion Z in real time after the detection of the side seam 176. But, in the disclosed embodiment, after the surface scanning is started, the obtained defect information is stored in the defect information memory 268 until the side seam 176 is detected. After completion of the surface scanning, the defect information stored in the memory 268 is read out and is collated with the mask pattern information from the memory 300B by the mask collating circuit 294, so that the defect information corresponding to the portion to be masked is actually masked or erased. In this case, since the surface scanning may be occasionally started just after the side seam, the memory 268 is required to have a capacity corresponding to one revolution of the paper cup.

The dimensions of cups are the same in the same kind of cups. Therefore, the image information corresponding to the upper edge 172 and the side-bottom seam 178 is easily masked by the main scanning direction defect information detecting circuit 264 on the basis of the reference axis signal from the main scanning direction reference axis setting circuit 274. The width of the portion to be masked can be determined on the basis of the dimensional accuracy of cups to be inspected so as to able to surely mask the upper edge and the side-bottom seam.

As mentioned above, it is possible to, after detection of the side seam 176, mask the image information corresponding to the upper inclined side seam 176A in real time by the mask pattern information from the reference memory 300A. But, if the scanning is started from the scanning line crossing the inclined side seam 176A, the side seam 176 cannot be detected unless the paper cup is rotated almost one revolution. In this case, after the detection of the side seam 176, if the masking operation for the inclined side seam 176A is performed and the defect detection processing is executed in real time for the whole surface of the paper cup, it takes a further one revolution of the cup before the processing is completed. In other words, the surface scanning is required over about two revolutions of the cup. The two revolutions of each cup makes the inspection time for each cup longer. Instead of this, information of one full picture may be stored in a memory, so that, after the completion of the scanning for the one full picture, the information in the memory is processed. In this case, it is sufficient if only the information of one full picture is obtained once, i.e., if the cup is rotated one revolution. But, there is required a memory capable of storing the information of one full picture.

Figure 32:
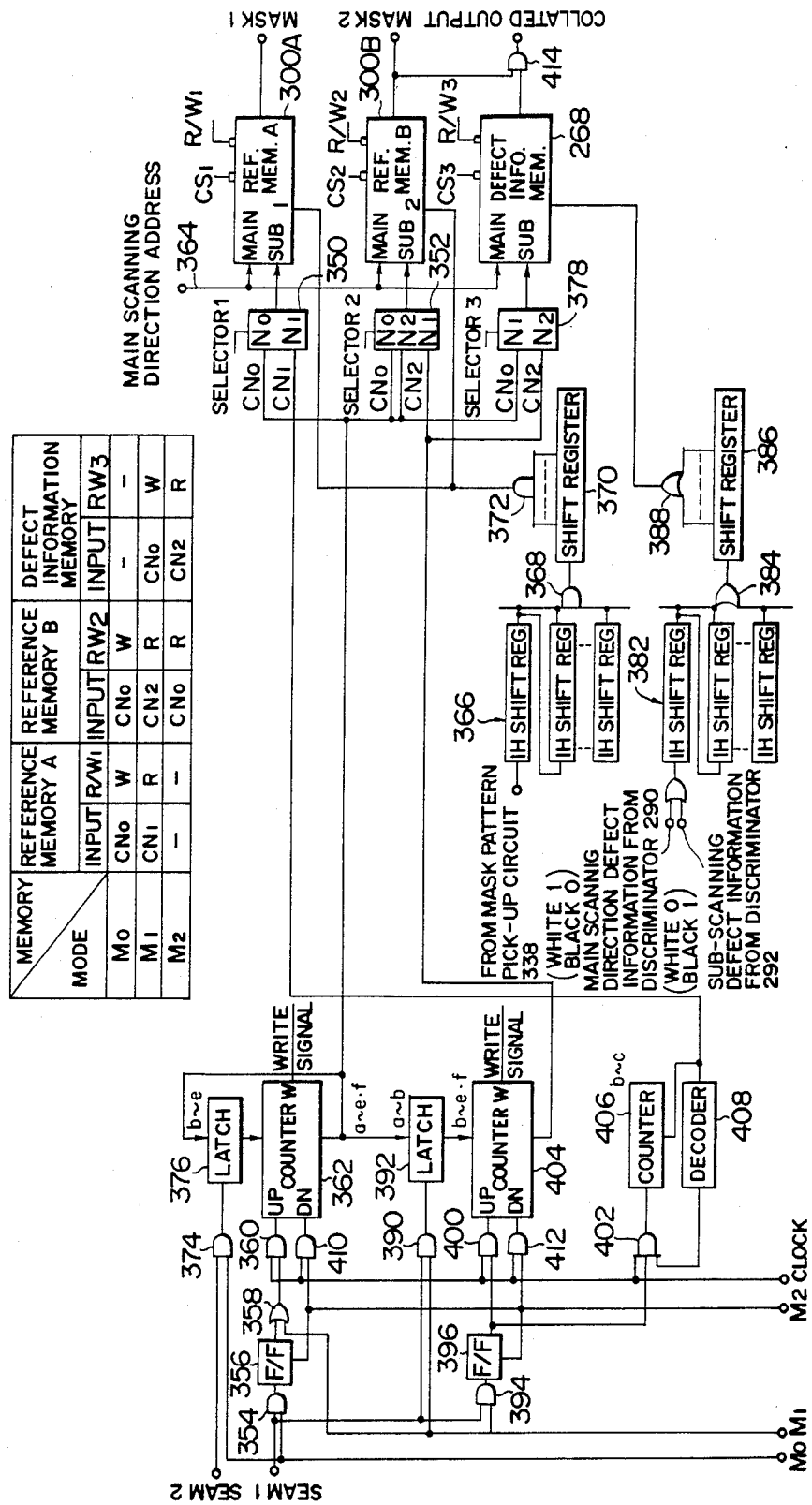
FIG. 32 is a circuit diagram of the mask pattern circuit.

The circuit shown in FIG. 32 is constructed to skilfully solve the above mentioned problems, so that the scanning for only about one full picture is sufficient and no memory for storing the information for one full picture is required. Namely, the start of the defect information detecting operation is ordinarily delayed from the start of the actual surface scanning operation by at least a predetermined period of time corresponding to the period from the time the vertical side seam is detected to the time the upper end of the inclined side seam is scanned. But, if the side seam is detected within the above predetermined period of time from the start of the actual surface scanning operation, the defect information detecting operation is started when the side seam is detected. In this case, even if the scanning is started from a scanning line crossing the upper inclined side seam 176A, the defect information detecting processing is started after the scanning line passes the inclined side seam 176. Therefore, the inclined side seam is always detected after the vertical side seam is detected. Accordingly, as will be explained in detail hereinafter, it is always possible to collate the image information corresponding to the inclined side seam portion with the mask pattern information from the reference memory 300A in real time when the vertical side seam 176 is detected. To the contrary, if the cup is scanned only for the time period in which the cup is rotated just one revolution, there is not defect-inspected the portion corresponding to the above predetermined time period from the start of the actual surface scanning operation to the start of the defect information detecting operation. Accordingly, when the cup is scanned, the cup is rotated more than one revolution, i.e., 360° plus the degree corresponding to the above predetermined time period, so that the completely overall inner surface of the cup is subjected to the defect inspection. Thus, the image information for the side surface can be always processed in real time irrespectively of the starting position of the actual surface scanning operation to the side seam 176.

As mentioned above, the bottom hole 180 has the constant positional relation to the side seam 176. But, the position of the hole is different in different kinds of cup. Therefore, the hole may be just behind the side seam or just before the side seam. Accordingly, the above method for the inclined side seam cannot be used for masking the image information corresponding to the hole 180. However, it is true that unless the reference axis such as the vertical side seam is found it is not possible to collate the obtained image information with the mask pattern for the hole. In addition, if the image information is collated with the mask pattern information in real time after the side seam is detected, it is necessary to further scan the cup the amount corresponding to one full picture after the detection of the side seam. Thus, in order to make the processing time as fast as possible, the disclosed embodiment is adapted so that it is sufficient if only the information corresponding to one full picture is obtained after the defect information detecting operation is started regardless of when the side seam is detected. Namely, the defect information obtained on the basis of the image information after the start of the actual surface scanning operation by the above mentioned predetermined period of time, is condensed and stored in the defect information memory. When the side seam is detected, the writing operation to address signal inputted to their respective Mo input terminals, to a pair of reference memories 300A and 300B, respectively. As will be explained in detail hereinafter, the memory 300A is adapted to store mask pattern information for the upper inclined portion 176A of the side seam, and the memory 300B is adapted to store mask pattern information for a mask pattern covering the side-bottom seam 178 and the bottom hole 180.

In this condition, the surface scanning operation is started regardless of the position of the side seam. Assume that the starting line of the surface scanning operation is the scanning line "a" in FIG. 31. With the advancement of the scanning operation, when the line-scanning is performed along the scanning line "b" passing over the side seam 176, the seam detecting circuit as shown in FIG. 29, which constitutes the sub-scanning direction reference axis setting circuit 272, outputs a high-level logical signal to an input labelled "SEAM 1". As a result, an AND gate 354 having a first input connected to the "SEAM 1" input and a second input connected to the command input Mo, supplies a high-level logic signal to a flip-flop 356 so as to set it. The output of the flip-flop is consequently brought to a high logical level, and is fed through an OR gate 358 to one input of an AND gate 360. This AND gate 360 receives at the other input thereof a clock signal of one pulse per one main scanning, and has an output connected to a count-up input of an up-down counter 362. Therefore, the counter 362 counts the address of each main scanning in the sub-scanning direction from the side seam. The count output of the counter 362 is supplied, as the sub-scanning direction address signal, through the mode selectors 350 and 352 to the reference memories 300A and 300B which are at this time put in a write mode by a read/write control line. These reference memories 300A and 300B also receive through a line 364 a main scanning direction address signal indicative of the address in the main scanning direction of each picture element signal.

On the other hand, the mask pattern information is supplied from the mask pattern pick-up circuit 338 through the phase adjusting circuit 340 to a shift register array 366 consisting of n shift registers of the N stages connected in series. The output of each shift register is connected to an AND circuit 368. The mask pattern information is composed of a high-level logical signal, i.e., the logic "1" indicative of the white and a low-level logical signal, i.e., the logic "0" indicative of the black.

Therefore, unless all the n picture elements in the sub-scanning direction indicate the white, the AND circuit 386 does not output the high-level logical signal. In other words, if one of the n picture elements in the sub-scanning direction indicates the black, the AND circuit 368 supplies the signal indicative of the black. Therefore, the extent of the black area, namely, the mask pattern is enlarged by the n picture elements in the sub-scanning direction.

The output of the AND circuit 368 is connected to a shift register 370 of the m stages, and the output of each stage of this shift register is connected to an AND circuit 372. With this arrangement, the mask pattern is enlarged by the m picture element in the main scanning direction. Therefore, the mask pattern is enlarged in the sub-scanning direction and in the main scanning direction by means of the circuit constituted of the shift register array 366, the shift register 370 and the AND circuits 368 and 372. This circuit is the mask pattern enlarging circuit 342 as shown in FIG. 13.

The enlarged mask pattern information is supplied from the AND circuit 372 to the reference memories 300A and 300B, respectively. Therefore, as mentioned above, the memory 300A starts to store the mask pattern information for the upper inclined portion 176A of the side seam, and the memory 300B starts to store the mask pattern information for the mask pattern covering the side-bottom seam 178 and the bottom hole 180. At this time, since these memories are maintained in the write mode as mentioned above, the mask pattern information is written into these memories. In this case, in order to reduce the required storage capacity of these memories, the information is condensed by using the addressing frequency of 1/m of the frequency of the image information. If the addressing frequency of such a value is used, the image information is written into the memories 300A and 300B at the rate of one of each m picture elements, so that the image information is condensed into 1/m. In the disclosed embodiment for the paper cup surface inspection, the mask pattern information is condensed to ¼.

With the further advancement of the scanning operation, when a predetermined number of scannings in the main scanning direction are performed after the side seam 176 is detected, namely, when the scanning is executed along a scanning line C slightly behind the upper end of the inclined side seam 176A, a write stopping signal is fed to a select input CS, of the memory 300A to cause it to terminate its writing operation. With this writing operation, the mask pattern information for the upper inclined seam 176 is stored in the memory 300A.

When the side seam 176 is detected again, the sub-scanning direction reference axis setting circuit 272 outputs a high-level seam detection signal from the output line labelled "SEAM 2" to one input of an AND gate 374 whose other input is connected to the mask pattern preparation command input Mo. As a result, a high-level signal is outputted from the AND gate 374 to a latch circuit 376, so that the latch circuit 376 stores the count value of the counter 362 at that time, which indicates the address of the final scanning line of the image obtained when the cup is rotated even just one revolution, namely, the length in the sub-scanning direction of the cup image obtained by rotating the cup just one revolution. Thereafter, when the scannings of the same number as the predetermined number mentioned above are performed after the second detection of the side seam 176, namely, when the scanning is executed along a scanning line "f" behind from the line "e" by the sub-scanning direction length of the mask pattern information stored in the memory 300A, a write stopping signal is supplied to selection input $CS_2$ of the memory 300B so as to terminate the writing operation of the memory 300B. With this, the mask pattern information for the side-bottom seam and the bottom hole is stored in the memory 300B. Therefore, all the necessary mask pattern information is stored in the memories 300A and 300B.

Next, explanation will given made of the defect information detection for the paper cup. Generally, it can be said that for a high speed defect information detecting operation it is necessary to process the obtained image information in real time to a maximum possible extent by making the obtained information stored in a buffer memory a little as possible. Here, referring to FIG. 31, the defect information memory is stopped, and thereafter, the defect information is collated in real time with the mask pattern information which is read out from the reference memory in the order of the address number. After the scanning for one full picture (one revolution plus the predetermined period of time as mentioned above) is completed, the defect information in the defect information memory is collated with the corresponding mask pattern information in the reference memory.

Next, explanation will be made of the specific embodiment of the defect information detecting operation with reference to FIGS. 31 and 32.

When the paper cup to be inspected is scanned while rotating it about its own axis. The detection circuit of reference axis becomes active and this high-level logical signal is supplied to a detected information storing command input $M_1$ of the mask pattern circuit, and the mode selectors 350 and 352 and a mode selector 378 associated with the defect information memory 268 are respectively set to supply the address signal inputted to their respective $N_1$ input terminals, to the reference memories 300A and 300B and the defect information memory 268, respectively. At this time these reference memories are put in a read mode, and the defect information memory is put in a write mode.

The high-level logical signal supplied to the input $M_1$ of the mask pattern circuit is fed through the OR gate 358 to the gate 360 whose other input is connected to the clock signal line. Therefore, the counter 362 starts to count the main scanning clocks, so that the count value of this counter indicates the address number of each main scanning in the sub-scanning direction. Since the output of the counter 362 is connected to the input $N_1$ of the mode selector 378, the address signal is supplied to the memory 268.

On the other hand, the defect information respectively outputted from the discriminating circuits 290 and 292 is combined by an OR circuit 380 and then is supplied to a shift register array 382 consisting of n shift registers of the N stages connected in series. The output of each shift register is connected to an OR circuit 384 whose output is connected to a shifter register 386 of the m stages. The output of each stage of this shift register 386 is connected to an OR circuit 388 having an output connected to the input of the defect information memory 268. This defect information is composed of a high-level logical signal, i.e., the logic "1" indicative of the black and a low-level logic signal, i.e., the logic "0" indicative of the white. Accordingly, if at least one of the outputs of the discriminating circuits 290 and 292 is the high-level logical signal indicative of the black, the output of the OR circuit 380 is also the high-level signal. This means that in such a case the picture element is regarded as being the black. In addition, if the high-level logical signal is inputted to at least one input of the OR circuit 384, the high-level signal is outputted from the OR circuit 384. This also means that if at least one of the n picture elements adjacent to one another in the sub-scanning direction indicates the black, all the n picture elements are regarded as being the black. If at least one of the stages of the shift register 386 outputs the high-level logical signal, the OR circuit 388 outputs the high-level signal. Therefore, if at least one of the m picture elements adjacent to one another in the main scanning direction is the black, all the m picture elements are treated as the black. Accordingly, the defect in the defect information is enlarged by the 2m picture elements in the main scanning direction and by the 2n picture elements in the sub-scanning direction. This is effective in preventing the defect information from disappearing when the defect information is condensed and stored in the memory 268. The defect information enlarged in such a manner is fed to and written into the memory 268. At that time, it is condensed by using the addressing frequency of 1/m of the frequency of the image information, similarly to the case of the writing of the mask pattern information into the reference memories.

In such a manner, the counter 362 counts up with the advancement of the scanning operation, and the defect information is stored in the defect information memory 268. At the first time detection of the side seam, i.e., at the scanning along the line "b" in FIG. 32, the sub-scanning direction reference axis setting circuit 272 outputs the high-level logical signal from its SEAM 1 output to the SEAM 1 input of the mask pattern circuit. The SEAM 1 input is connected to one input of an AND gate 390 whose other input is connected to the detected information storing command input $M_1$. Therefore, the AND gate 390 outputs the high-level signal to a latch circuit 392 to cause it to store the count value of the counter 362 indicating at that time the address in the sub-scanning direction of the side seam in the defect information memory 268.

The high-level signal is also fed from the SEAM 1 input to the one input of an AND gate 394 whose other input is connected to the storing command input $M_1$. Therefore, a high-level signal is also fed from the AND gate 394 to a flip-flop 396 to put it into a set condition. The flip-flop 396 in the set condition supplies a high-level logical signal to one input of an AND gate 400 adapted to receive the clock signal at the other input and having its output connected to a count-up input of a up-down counter 404. Thus, the counter 404 starts to count the address in the sub-scanning direction beginning from the side seam. The output of the flip-flop also supplies the high-level logical signal to a first input of an AND gate 402 which has a second input connected to the clock input, a third input connected to an output of a decoder 408 and an output connected to a counter 406. Therefore, the counter 406 also starts to count the address in the sub-scanning direction beginning from the side seam. Thus, the count outputs of the counters 406 and 404 are supplied through the $M_1$ inputs of the mode selectors 350 and 352 to the reference memories 300A and 300B, respectively, as the address signal indicative of the address number in the sub-scanning direction beginning from the side seam.

As mentioned above, the reference memories 300A and 300B are in a read mode at this time, the mask pattern information is read from the memories in accordance with the address numbers supplied from the counters 406 and 404, and is supplied to the discriminating circuits 290 and 292. Accordingly, these discriminating circuits collate the defect information with the mask pattern information in real time from the line "b" toward the right in FIG. 31, so as to output to the total discriminating circuit 276 the defect information that has not been masked by the mask pattern.

As mentioned hereinbefore, the defect information is composed of the high-level logical signal indicative of the black and the low-level logical signal indicative of the white, and the mask pattern information is composed of the low-level logical signal indicative of the black and the high-level logical signal indicative of the white. Namely, the defect information is opposite to the mask pattern information in the logical format showing the black and white. Accordingly, in the discriminating circuits, if the logical product between the mask pattern information and the defect information is sought, only the true defect information can be obtained. Specifically, if the mask pattern information is the low-level logical signal indicative of the black, the logical product between the mask pattern information and the defect information becomes the low-level logical signal indicative of the white. Namely, the defect information is masked or erased. On the other hand, if the mask pattern information is the high-level logical signal indicative of the white, the logical product is determined only by the defect information. If the defect information is the high-level logical signal indicative of the black, the logical product is also the high-level. Namely, the defect information is not masked, and it is finally discriminated to be a defect.

When the counter 406 reaches a count value at which all the information in the memory 300A is read out, the decoder 408 outputs a low-level signal to the AND gate 402 so as to close the gate, so that the counter 406 stops counting up.

With further advancement of the scanning operation, when the surface scanning of the amount corresponding to one revolution of the paper cup plus the capacity of the reference memory 300A is completed, namely, when the scanning is performed along the line "d" in FIG. 31, the signal supplied to the detected information storing command input $M_1$ is brought to a logical low-level, and a high-level logical signal is supplied to a post-processing command input $M_2$. With this, the real time processing in the discriminating circuit is completed. In addition, the mode selectors 352 and 378 are set to supply the address signal inputted to their input $M_2$ to the reference memory 300B and the defect information memory 268.

With application of the high-level signal to the post-processing command input $M_2$, the flip-flops 356 and 396 are reset, and at the application of the low-level signal to the detected information storing command input $M_1$, the AND gates 360 and 400 are closed to cause the associated counters 362 and 404 to stop their count-up operation. Then, a write signal is supplied to the counters 362 and 404 so as to clear these counters and to write the address number of the second detected side seam in the mask pattern information stored in the latch circuit 376, to the counter 362, and the address number of the first detected side seam in the defect information stored in the defect information memory 268, to the counter 404. On the other hand, the high-level signal supplied to the command input $M_2$ is also fed to one input of AND gates 410 and 412 whose other inputs are connected to the clock input and whose outputs are connected to count-down inputs of the counters 362 and 404, respectively. Therefore, the counters 362 and 404 start to count down at each clock signal from the respective written address numbers. The decreasing address numbers supplied from the counters 362 and 404 are respectively fed to the reference memory 300B and the defect information memory 268. As a result, in the reference memory 300B the mask pattern information is read out from the scanning line "e" toward the left in FIG. 31 and is then fed to an AND circuit 414, and in the defect information memory 268 the defect information is read out from the scanning line "b" toward the left in FIG. 31 and is also fed to the same AND circuit 414. This AND circuit 414 supplies the high-level signal indicative of only the defect information that has not been masked by the mask pattern at the left side of the side seam. Therefore, this AND circuit 414 constitutes the mask collation circuit 294. This collating operation continues until the count value in the counter 404 and hence the address number of the defect information in the memory becomes zero. With this, the defect information between the scanning lines "a" and "b" in FIG. 31 is collated with the mask pattern information between the scanning lines "d" and "e". As a result, the defect information between the scanning lines "a" and "d" is masked by the mask pattern information between the scanning line "d" and "e" and between the scanning lines "b" and "d".

In accordance with the above mentioned system, the obtained image information can be collated with the mask pattern if only one scanning operation is performed to obtain one full picture irrespectively of the starting position of the scanning to the reference axis. Therefore, the time required to surface-scan the product to be inspected can be reduced. This enables a high speed surface inspection. This is also effective when each product to be inspected can be imaged only once, for example when products to be inspected having a portion to be masked in a constant positional relation to the reference axis are located in random directions and are conveyed by a conveyer driven in one direction.

The total discriminating circuit 276 receives the defect information from the main scanning direction discriminating circuit 290, the sub-scanning direction discriminating circuit 292 and the mask collating circuit 294 and totally determine whether the product inspected in the above mentioned manner is defective or non-defective. The output of this circuit 276 is supplied to the display device 204 and the separation control device 206. The total discriminating circuit 276 may be constructed by an OR circuit to output a defect signal when the defect information is outputted from at least one of the two discriminating circuits and the mask collating circuit. But, if the respective outputs of the discriminating circuits and the mask collating circuit indicate the amount of the defect, the total discriminating circuit may be constructed to seek the total value of the defect information and to compare it with a reference value so as to determine that the product is defective when the total value exceeds the reference value.

Figure 33:
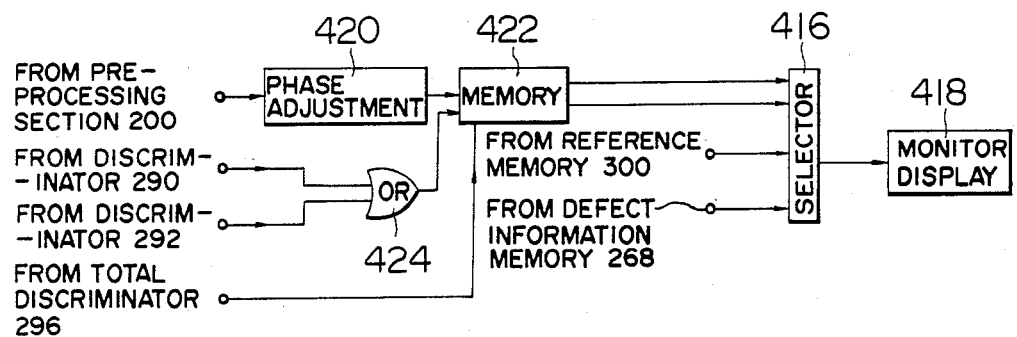
FIG. 33 is a block diagram of a display apparatus.

The display device 204 may include a printer for printing out the number of defects on each defective product or the total amount of the defects, and a video display for the image of the defective product. The form or type of the display device can be suitably determined in accordance with a user's need and any form or type of display device can be easily constructed on the basis of well-known techniques. For example, as shown in FIG. 33, the display device may be constructed of a selector 416 adapted to cause a monitor video display 418 selectively display the pre-processed image, the image of the defect portion, the mask pattern and the full picture of the defective cup. The pre-processed image information is phase-adjusted by a phase adjusting circuit 420 and is stored in a memory 422 once. The image information is then outputted from the memory 422 through the selector 416 to the video display. If the sequentially inspected products are non-defective, it is preferable to display the detected image by the video display 418.

The defect information from the discriminating circuits 290 and 292 is combined by an OR circuit 424 and is sequentially stored in the memory 422. When the total discriminating circuit 276 outputs the defect signal, the total discriminating circuit 276 also outputs a control signal to the memory 422 so as to cause it to supply a processed image of only the defect portion, in place of the pre-processed image, to the selector 416, so that the image of the defect portion is displayed for a predetermined period of time. If necessary, a still picture image of the defective portion is displayed by manual operation of the selector 416. When an operator wishes to inspect the mask pattern, the mask pattern can be displayed by manually operating the selector. If an operator wishes to view the whole defect pattern of the cup found as defective and to obserse distribution of the defect portions, the defect-emphasized full picture image of the cup surface can be displayed by a manual operation of the selector. But, since the full picture image is a condensed image, when one wishes to inspect the defect by a detailed image, it is necessary to display the image of only a defect portion in question.

Figure 34:
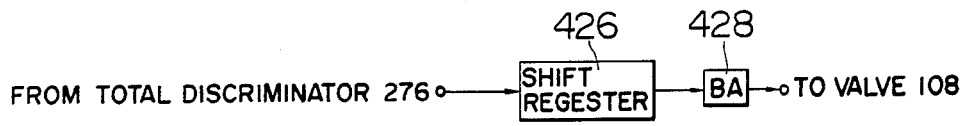
FIG. 34 is a block diagram of a control device for rejecting a defective paper cup.

Separation of the defective product and the non-defective product is performed by the separation control circuit 206 on the basis of the defect signal from the total discriminating circuit 276. But, since the time from the inspection of each product to the actual separation of the inspected products depends upon the construction of the actual system, it is necessary to design the separation control device 206 so as to fulfill the condition required by the actual system, but it is possible to do so on the basis of well-known technique. In the disclosed embodiment, as mentioned hereinbefore, the paper cup conveying apparatus has the circular indexing table provided with the six cup holders at its periphery. Each cup holder is intermittently rotated about the rotating axis of the index table one-sixth of rotation, and at the same time is continuously rotated about its own axis. During the rest period of the intermittent orbital rotation of the cup holders, there are performed various operations including the supply of the paper cup, the pushing of the supplied paper cup, the inspection of the paper cup, the ejection of the defective cup and the feed-out of the non-defective cup. Therefore, for example, as shown in FIG. 34, the separation control device 206 is constructed by a two-stage shift register 426 adapted to receive the discrimination signal from the total discriminating circuit 276 and a buffer and drive amplifier 428 having an input connected to the output of the shift register 426 and an output connected to the value 108 for energizing the valve 108. During each rest period of the intermittent orbital rotation of the cup holders, the discrimination signal (the high-level signal indicative of a defective or the low-level signal indicative of a non-defective) is outputted from the total discriminating circuit 276 to the shift register 426, and on the other hand the shift register 426 outputs the discrimination signal inputted thereto two rest periods before. In other words, when each inspected cup reaches the defective product ejecting station from the inspection station, the shift register 426 outputs the discrimination signal on the cup which just reached the ejecting station. Therefore, if the cup in the ejecting station had been determined as being defective, the shift register 426 outputs the high-level signal to the buffer and drive amplifier 426 so as to cause it to energize the valve 108, so that the cup is ejected by the compressed air. To the contrary, if the cup in the ejecting station had been determined as being non-defective, since the shift register 426 outputs the low-level signal, the buffer and drive amplifier 426 does not energize the valve 108. In this case, when the cup reaches the feed-out station, the cup is fed as a non-defective cup.

In the above mentioned embodiment, if so high speed processing is not required, the defect information memory 268, the mask collating circuit 294 and the defect information condensing circuit 298 may be omitted. In this case, the system is constructed so that after detection of the side seam, the paper cup is rotated further one revolution so as to able to collate the defect information of the amount corresponding to one revolution obtained after the detection of the side seam, with the mask pattern from the reference memory in real time. If the system is constructed as mentioned above, it is necessary to rotate the cup about two revolutions at maximum from the start of the surface scanning to the completion of the defect information processing, but it is advantageous in that a memory for defect information is not necessary.

The automatic surface inspection system in accordance with this invention can be used not only for the inner surface inspection of the paper cup as mentioned above but also for inspection of the surface of other products.

Figure 35:
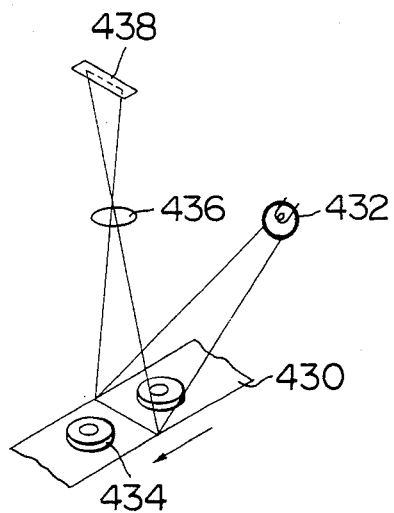
FIG. 35 is a diagrammatic view showing the manner for detecting the surface of objects conveyed by a belt conveyer.

For example, the automatic surface inspection system can be used for inspection of the surface of a circular product 434 as shown in FIG. 35, which is continuously conveyed by a belt conveyor 430 driven at a constant speed and is uniformly illuminated by a light source 432. In this case, the linear sensor array 438 is located perpendicularly to the conveying direction of the conveyor 430, so that the product 434 can be surface-scanned by repeatedly scanning the linear sensor array. The scanning direction of the linear sensor array is the main scanning direction, and the conveying direction of the conveyor 430 is the sub-scanning direction. Therefore, by applying the output of the linear sensor array 438 to the pre-amplifier 210 of the system shown in FIG. 13, similar surface inspection can be performed for the product 434.

When each product can be surface-scanned only once as in the case that the surface inspection has to be made for a product conveyed in one direction by a belt conveyor and the like as mentioned above, this automatic surface inspection system having the defect information memory and the mask collating circuit is very effective since it can perform the defect detecting operation while executing necessary masking treatment on the basis of only one picture image obtained by one surface-scanning.

The automatic surface inspection system can be also used for inspecting the surface of a stationary product. In this case, the stationary product is surface-scanned by a suitable conventional manner, and the obtained image signal is supplied to the pre-amplifier 210.

As mentioned above, since the automatic surface inspection system in accordance with this invention can make necessary mask treatment on the edge and the seam of a product to be inspected and at the same time does not completely mask the edge and the seam along either the main scanning direction or the sub-scanning direction, it can detect only defects to a very small defect.

The invention has thus been shown and described with reference to specific embodiments. However, it should be noted that the invention is in no way limited to the details of the illustrated structures but changes and modifications may be made without departing from the scope of the appended claims.

I claim:

1. An automatic surface inspection system comprising:

a surface scanning means for scanning the surface of an object to be inspected in main and sub-scanning directions, to output an analog picture element signal in each scanning direction;

a processing means having a pre-processing section adapted to receive said analog picture element signal from said surface scanning means for shaping said signal and converting it into a digital picture element signal, and a data processing section receiving said digital picture element signal from said pre-processing section for conducting surface inspection;

said data processing section including:

a first reference axis setting circuit adapted to receive said digital picture element signal from said pre-processing section for detecting a reference axis in the main scanning direction;

a second reference axis setting circuit receiving said digital picture element signal from said pre-processing section for detecting a reference axis in the sub-scanning direction;

a mask pattern circuit adapted to receive said digital picture element signal from said pre-processing section and the first and second reference axis information to produce mask pattern information on portions thereof which are not to be subjected to the surface inspection and storing the information in a reference memory;

a first detecting circuit having a first discriminating circuit receiving said digital picture element signal and said first and second reference axis information for conducting a surface inspection in the main scanning direction to produce a first defect signal while receiving said mask pattern information from said mask pattern circuit to make necessary masking treatment in the main scanning direction;

a second detecting circuit having a second discriminating circuit adapted to receive said digital picture element signal and said first and second reference axis information for conducting a surface inspection in the sub-scanning direction to produce a second defect signal while receiving said mask pattern information from said mask pattern circuit to make necessary masking treatment in the sub-scanning direction;

a defect information memory for storing said first and second defect signals until the second reference axis is detected;

a mask collation circuit for reading said first and second defect signals and masking the signals in accordance with the mask pattern information from the reference memory; and a total discriminating circuit adapted to receive the signals from said first and second discriminating circuits and an output from said collation circuit for deciding whether or not the surface of said object inspected is acceptable or defective.

2. An automatic surface inspection system as defined in claim 1 in which said second reference axis setting circuit is adapted to sum all digital picture element signals for each main scanning line, to obtain a dynamic average value on each sum value in the sub-scanning direction, to compare the dynamic average value with the sum value so as to seek the difference between the dynamic average value and the sum value, and to compare the difference with a predetermined value so as to determine, as the reference line, a scanning line of that sum value between which and the dynamic average value the difference is not less than said predetermined line.

3. An automatic surface inspection system as defined in claim 1 in which said first reference axis setting circuit is adapted to detect, as a reference line, the portion where the picture element signal firstly changes from the condition representing the dark to the condition representing the light after the start of each scanning.

4. An automatic surface inspection system as defined in claim 1 in which said pre-processing section has an outline-emphasizing and smoothening circuit which includes a first adder adapted to obtain the sum "g" of digital picture element signals of four picture elements adjacent in vertically and horizontally to each picture element corresponding to each digital picture element signal "E", a second adder adapted to obtain the sum "$g_2$" of digital picture element signals of four picture elements adjacent in upper-right, upper-left, lower-right and lower-left directions to said picture element corresponding to said digital picture element signal "E", a first operational circuit receiving said sums "$g_1$" and "$g_2$" to output, as peripheral data "g", either the sum "$g_1$" or the average value $(g_1+g_2)/2$, a coefficient circuit supplying a weighting coefficient "K", a second operational circuit receiving said peripheral data "g", said weighting coefficient "K" and said digital picture element signal "E" for seeking an outline emphasizing signal $((K+4)E-g)/K$ and a smoothened signal $(KE+g)/K+4)$, and an output selection circuit for selectively outputting either said outline emphasizing signal or said smoothened signal.

5. An automatic surface inspection system as defined in claim 1 in which each of said first and second detecting circuits has a defect information pick-up circuit adapted to seek a dynamic average value on each inputted digital picture element signal in the scanning direction, to obtain a first difference signal between the dynamic average value and the inputted digital picture element signal, to compare said first difference signal with a first low threshold level so as to sense a defective portion of a relatively high concentration, to obtain a second dynamic average value of each of said difference signals, to compare said second dynamic average value with a second threshold level so as to sense an area where a defective portion of a relatively low concentration exists, to enlarge the extent of said area, and to compare a third high threshold level with said difference signal within said enlarged area so as to sense the defective portion of a relatively low concentration.

6. An automatic surface inspection system as defined in claim 5 in which the threshold levels are predetermined such that in detection of defective portions a mask processing is not performed in the scanning direction along which a portion to be masked exists but performed in the scanning direction perpendicular to said scanning direction along which said portion to be masked exists, so that the portion to be masked is not detected as a defective portion but a defective portion existing around the portion to be masked is effectively detected, if any.

7. An automatic surface inspection system as defined in claim 1 in which said detecting circuit is adapted to start its detecting operation with a delay of the time corresponding to the sub-scanning direction length of a mask pattern for a small portion to be masked which exists behind and close to the sub-scanning direction reference axis, for the start of scanning operation for the surface of the object to be inspected.

8. An automatic surface inspection system as defined in claim 1 or 5 in which said mask collation circuit reading, after completion of the scanning operation for the surface of the object to be inspected, said first and second defect signals and outputting only inspection information on a portion which should not be masked.

9. An automatic surface inspection system as defined in claim 8 in which said mask collation circuit reads and masks in the order of high address number to low address number.

10. An automatic surface inspection system as defined in claim 1 in which said object to be inspected is a paper cup and which further includes a conveying apparatus having an intermittently driven rotary indexing table and a plurality of cup holders located at a periphery of said indexing table and adapted to continuously rotated about their own axis.

11. An automatic surface inspection system as defined in claim 10 in which each of cup holder is connected to a planetary gear in mesh with a sun gear which rotatably and coaxially mounted on a rotating shaft of said indexing table and adapted to be driven independently of said shaft of said indexing table.

12. An automatic surface inspection system as defined in claim 1 or 10 in which said surface scanning means is a linear sensor array located at a position obliquely above the object to be inspected, said object to be inspected being rotated about its own axis.

13. An automatic surface inspection system comprising:
    a surface scanning means for scanning the surface of an object to be inspected to output an analog picture element signal in each scanning direction;
    a processing means having a pre-processing section adapted to receive said analog picture element signal from said surface scanning means for shaping said signal and converting it into a digital picture element signal;
    a data processing section, being part of said processing means and receiving said digital picture element signal from said pre-processing section for conducting surface inspection;
    said data processing section including:
    a reference axis setting circuit adapted to receive said digital picture element signal from said pre-processing section for detecting a reference axis in the sub-scanning direction;
    a first detecting circuit having a first discriminating circuit adapted to receive said digital picture element signal for conducting a surface inspection in the main scanning direction to produce a first defect signal while receiving said mask pattern information from said mask pattern circuit to make necessary masking treatment in the main scanning direction
    a second detecting circuit having a second discriminating circuit adapted to receive said digital picture element signal and the reference axis information for conducting a surface inspection in the sub-scanning direction to produce a second defect signal while receiving said mask pattern information from said mask pattern circuit to make necessary masking treatment in the sub-scanning direction;
    a defect information memory for storing said first and second defect signals until the reference axis is detected;
    a mask collation circuit for reading said first and second defect signals and masking the signals in accordance with the mask pattern information from the reference memory; and,
    a total discriminating circuit adapted to receive the signals from said first and second discriminating circuits and an output from said collation circuit for deciding whether or not the surface of said object inspected is acceptable or defective.

14. An automatic surface inspection system as defined in claim 13 in which said second reference axis setting circuit is adapted to sum all digital picture element signals for each main scanning line, to obtain a dynamic average value on each sum value in the sub-scanning direction, to compare the dynamic average value with the sum value so as to seek the difference between the dynamic average value and the sum value, and to compare the difference with a predetermined value so as to determine, as the reference line, a scanning line of that sum value between which and the dynamic average value the difference is not less than said predetermined line.

15. An automatic surface inspection system as defined in claim 13 in which said detecting circuit is adapted to start its detecting operation with a delay of the time corresponding to the sub-scanning direction length of a mask pattern for a small portion to be masked which exists behind and close to the sub-scanning direction reference axis, from the start of scanning operation for the surface of the object to be inspected.

16. An automatic surface inspection system as defined in claim 13 or 15 in which said mask collation circuit reads, after completion of the scanning operation for the surface of the object to be inspected, and masks so as to output only information on a portion which should not be masked.

* * * * *